(12) United States Patent
Tran

(10) Patent No.: US 10,041,865 B2
(45) Date of Patent: Aug. 7, 2018

(54) CORNEAL TISSUE SAMPLE ASSEMBLIES AND RELATED METHODS OF USE

(71) Applicant: Lions VisionGift, Portland, OR (US)

(72) Inventor: Khoa D. Tran, Portland, OR (US)

(73) Assignee: LIONS VISIONGIFT, Portland, OR (US)

( * ) Notice: Subject to any disclaimer, the term of this patent is extended or adjusted under 35 U.S.C. 154(b) by 0 days.

(21) Appl. No.: 15/874,789

(22) Filed: Jan. 18, 2018

(65) Prior Publication Data

US 2018/0143109 A1    May 24, 2018

Related U.S. Application Data

(63) Continuation of application No. 15/660,004, filed on Jul. 26, 2017.

(60) Provisional application No. 62/407,930, filed on Oct. 13, 2016.

(51) Int. Cl.
| | | |
|---|---|---|
| *G01N 1/28* | (2006.01) | |
| *G01N 21/03* | (2006.01) | |
| *G01N 15/10* | (2006.01) | |
| *G01N 15/14* | (2006.01) | |

(52) U.S. Cl.
CPC .............. *G01N 1/28* (2013.01); *G01N 15/10* (2013.01); *G01N 21/03* (2013.01); *G01N 2015/1006* (2013.01); *G01N 2015/1486* (2013.01); *G01N 2021/0342* (2013.01)

(58) Field of Classification Search
CPC ... G01N 1/28; G01N 21/03; G01N 2021/0342
See application file for complete search history.

(56) References Cited

U.S. PATENT DOCUMENTS

| | | |
|---|---|---|
| 6,605,093 B1 | 8/2003 | Blake |
| 2009/0270876 A1 | 10/2009 | Hoffmann et al. |
| 2010/0256651 A1 | 10/2010 | Jani et al. |

FOREIGN PATENT DOCUMENTS

EP          2 533 724 B1      11/2011

OTHER PUBLICATIONS

Eye Bank Association of America. 2015 Eye Banking Statistical Report. Washington D.C.: Eye Bank Association of America, 2016., EBAA: pp. 1-98.
Eye Bank Association of America. 2016 Eye Banking Statistical Report. Washington D.C.: Eye Bank Association of America, 2017., EBAA: pp. 1-99.
Eye Bank Association of America. 2016 Medical Standards. Washington D.C.: Eye Bank Association of America, 2016., EBAA: pp. 1-67.

(Continued)

*Primary Examiner* — Kara D Johnson
(74) *Attorney, Agent, or Firm* — Stoel Rives LLP; Zhi-Xiang (Alex) Oh

(57) ABSTRACT

Assemblies for storing, handling, transporting, viewing, evaluating, and/or shipping corneal tissue are provided. The assemblies may include a viewing chamber and a corneal tissue carrier removably coupled to an inner portion of the viewing chamber. The assemblies may further include a corneal tissue sample disposed within the corneal tissue carrier. Methods of processing a corneal tissue sample and administering the corneal tissue sample to a subject are also provided.

30 Claims, 13 Drawing Sheets

(56) References Cited

OTHER PUBLICATIONS

R Project: A language and environment for statistical computing. [computer program]., Vienna, Austria: R Foundation for Statistical Computing; 2010; version 3.2.4 http://www.r-project.org.

Anshu, et al., Risk of Corneal Transplant Rejection Significantly Reduced with Descemet's Membrane Endothelial Keratoplsty, Elsevier, Inc. American Academy of Ophthalmology, 2012, pp. 536-540.

Deng, et al., Clinical Outcomes of Descemet Membrane Endothelial Keratoplasty Using Eye Bank-Prepared Tissues, American Journal of Ophthalmology. Mar. 2015: pp. 590-596.

Guerra, et al., Descemet's Membrane Endothelial Keratoplasty: Prospective Study of 1-Year Visual Outcomes, Graft Survival, and Endothelial Cell Loss, Elsevier, Inc. American Academy of Ophthalmology. 2011: pp. 2368-2373.

Guerra, et al., Endothelial Keratoplasty: Fellow Eyes Comparison of Descemet Stripping Automated Endothelial Keratoplasty and Descemet Membrane Endothelial Keratoplasty, Cornea. Lippincott Williams & Wilkins. vol. 30, No. 12, Dec. 2011: pp. 1382-1386.

Ham, et al., Visual Rehabilitation Rate After Isolated Descemet Membrane Transplantation, American Medical Association. vol. 127, No. 3, Mar. 2009: pp. 252-255.

Hamzaoglu, et al., The First 100 Eyes of Standardized Descemet Stripping Automated Endothelial Keratoplasty versus Standardized Descemet Membrane Endothelial Keratoplasty., Elsevier, Inc. American Academy of Ophthalmology. 2015: pp. 2193-2199.

Holiman, et al., An Eye Bank DMEK Tissue Preparation Program for Corneas Stored at 4° C., 2015 Nova Science Publishers, Inc.: pp. 123-139.

Jardine, et al., Imaging and Quantification of Endothelial Cell Loss in Eye Bank Prepared DMEK Grafts Using Trainable Segmentation Software., Current Eye Research, Mar. 2014: pp. 894-901.

Liarakos, et al., Intraocular Graft Unfolding Techniques in Descemet Membrane Endothelial Keratoplasty, JAMA Ophthalmol, vol. 131, No. 1, Jan. 2013: pp. 29-35.

Majmudar, et al., Enhancing DMEK Success by Identifying Optimal Levels of Trypan Blue Dye Application to Donor Corneal Tissue, Wolters Kluwer Health, Inc. vol. 0, No. 0, Month 2016: pp. 1-5.

Melles, et al., Descemet Membrane Endothelial Keratoplasty (DMEK)., Cornea. Lippincott Williams & Wilkins. vol. 25, No. 8, Sep. 2006: pp. 987-990.

Melles,, et al., Transplantation of Descemet's Membrane Carrying Viable Endothelium Through a Small Scleral Incision, Cornea. Lippincott Williams & Wilkins, Inc. vol. 21, No. 4, 2002: pp. 415-418.

Parekh, et al., Preloaded Tissues for Descemet Membrane Endothelial Keratoplasty., American Journal of Ophthalmology, vol. 166, 2016: pp. 120-125.

Price, et al., Descemet Membrane Endothelial Keratoplasty, International Ophthalmology Clinics. vol. 50, No. 3, 2010: pp. 137-147.

Schallhorn, et al., Quantification and Patterns of Endothelial Cell Loss Due to Eye Bank Preparation and Injector Method in Descemet Membrane Endothelial Keratoplasty Tissues, Wolters Kluwer Health, Inc. vol. 35, No. 3, Mar. 2016: pp. 377-382.

Schindelin, et al., Fiji: an open-source platform for biological-image analysis., Nature Methods, vol. 9, No. 7, Jul. 2012: pp. 676-682.

Terry, et al., Standardized DMEK Technique: Reducing Complications Using Prestripped Tissue, Novel Glass Injector, and Sulfur Hexafluoride (SF6) Gas., Wolters Kluwer Health, Inc. vol. 34, No. 8, Aug. 2015: pp. 845-852.

Tourtas, et al., Descemet Membrane Endothelial Keratoplasty Versus Descemet Stripping Automated Endothelial Keratoplasty, Elsevier, Inc. American Journal of Ophthalmology. Jun. 2012: pp. 1082-1090.e2.

Tran, et al., Evaluation and Quality Assessment of Prestripped, Preloaded Descemet Membrane Endothelial Keratoplasty Grafts., vol. 36, No. 4, Apr. 2017: pp. 484-490.

Veldman, et al., Stamping an S on DMEK Donor Tissue to Prevent Upside-Down Grafts: Laboratory Validation and Detailed Preparation Technique Description., Wolters Kluwer Health, Inc. vol. 34, No. 9, Sep. 2015: pp. 1175-1178.

Wilcoxon, et al., Individual Comparisons of Grouped Data by Ranking Methods., Journal of Economic Entomology, vol. 39, No. 2, 1946: pp. 269-270.

Yoeruek, et al., Novel Maneuver Facilitating Descemet Membrane Unfolding in the Anterior Chamber., vol. 32, No. 3, Mar. 2013: pp. 370-373.

Zeidenweber, et al., Prestained and Preloaded DMEK Grafts: An Evaluation of Tissue Quality and Stain Retention, Wolters Kluwer Health, Inc. vol. 0, No. 0, Month 2017: pp. 1-6.

Preliminary Amendment dated Apr. 4, 2018 for U.S. Appl. No. 15/660,004.

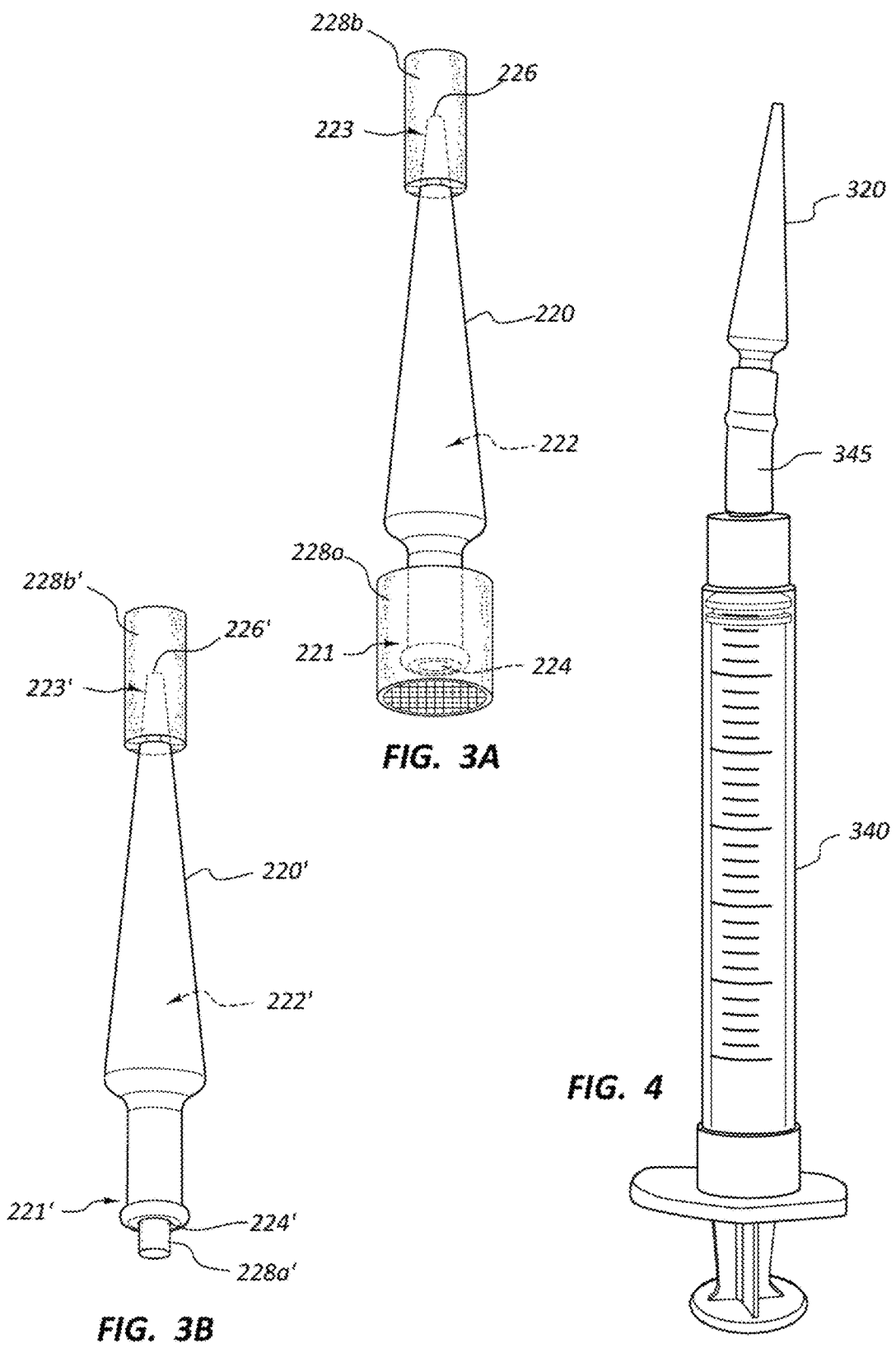

CORNEAL TISSUE SAMPLE ASSEMBLIES AND RELATED METHODS OF USE

CROSS-REFERENCE TO RELATED APPLICATIONS

This application is a continuation of U.S. application Ser. No. 15/660,004, filed Jul. 26, 2017, which claims the benefit and priority of U.S. Provisional Application No. 62/407,930, filed Oct. 13, 2016; the entire contents of each of the foregoing applications are hereby incorporated by reference herein.

TECHNICAL FIELD

The present disclosure relates generally to corneal tissue sample assemblies. More specifically, the present disclosure relates to corneal tissue sample assemblies for storing, handling, transporting, viewing, and/or evaluating corneal tissue. The present disclosure also relates to methods of processing corneal tissue samples and administering corneal tissue samples to subjects in need thereof.

BACKGROUND

Descemet membrane endothelial keratoplasty (DMEK) is a corneal transplantation procedure that enables a one-for-one replacement of a diseased Descemet membrane and endothelium complex (see Melles G R, et al. *Cornea*. 2002; 21:415-418; Melles G R, et al. *Cornea*. 2006; 25:987-990; and Price M O, et al. *Int Ophthalmol Clin*. 2010; 50:137-147). DMEK may provide improved post-operative visual outcomes, faster recovery times, and reduced rates of rejection compared to other endothelial keratoplasty procedures such as Descemet stripping automated endothelial keratoplasty (DSAEK) and penetrating keratoplasty (PK) (see Hamzaoglu E C, et al. *Ophthalmology*. 2015; Anshu A, et al. *Ophthalmology*. 2012; 119:536-540; Guerra F P, et al. *Ophthalmology*. 2011; 118:2368-2373; Tourtas T, et al. *Am J Ophthalmol*. 2012; 153:1082-1090 e1082; Guerra F P, et al. *Cornea*. 2011; 30:1382-1386; and Ham L, et al. *Arch Ophthalmol*. 2009; 127:252-255). While DSAEK and PK remain the most widely performed corneal transplant procedures worldwide, DMEK is steadily gaining ground on these and other surgical procedures in the United States (see Eye Bank Association of America. 2016 *Eye Banking of America Statistical Report*. Washington D.C.: Eye Bank Association of America; 2017).

With DMEK gaining popularity among surgeons, eye banks have developed internal processing programs to assist surgeons in preparing DMEK grafts (see Eye Bank Association of America. 2016 *Eye Banking of America Statistical Report*. Washington D.C.: Eye Bank Association of America; 2017; Holiman J, et al. In: Mohit Parekh.; Stefano Ferrari D P, ed. *Eye Banking*: Nova Biomedical; 2015:123-139; Deng S X, et al. *Am J Ophthalmol*. 2015; 159:590-596; and Terry M A, et al. *Cornea*. 2015; 34:845-852). Eye bank prepared pre-stripped tissues can help reduce both time in the operating room (OR) and potential complications that may arise if tissue preparation fails during surgery. Pre-stripped tissues can also provide an additional level of quality assurance as eye banks can perform post-processing evaluation of grafts using tissue evaluation instruments and methods, such as, specular microscopy, slit-lamp biomicroscopy, light microscopy, and/or optical coherence tomography, which are not typically performed in the OR. In the United States, the current Eye Bank Association of America (EBAA) Medical Standards (see Eye Bank Association of America. 2016 *Medical Standards*. Washington D.C.: Eye Bank Association of America; 2016) require that all eye bank prepared grafts be evaluated by specular microscopy and slit-lamp biomicroscopy.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 3A is a perspective view of a corneal tissue carrier.

FIG. 3B is a perspective view of another embodiment of a corneal tissue carrier.

FIG. 4 is a perspective view of a corneal tissue carrier coupled to a syringe.

indicates possible touch damage sustained during tissue manipulation. The image at the bottom left is of the DMEK graft depicted in the image at the top left, after pre-stripping and trephination, and prior to loading into a corneal tissue carrier. Panel C is a close-up image of damage caused by peeling of tissue. Panel D is a close-up image of damage caused by scraping against the glass corneal tissue carrier. Panel E is a close-up image of edge damage due to trephination. Panel F is a close-up image of a touch defect, possibly caused during tissue loading or unfurling for analysis.

Figure 9:
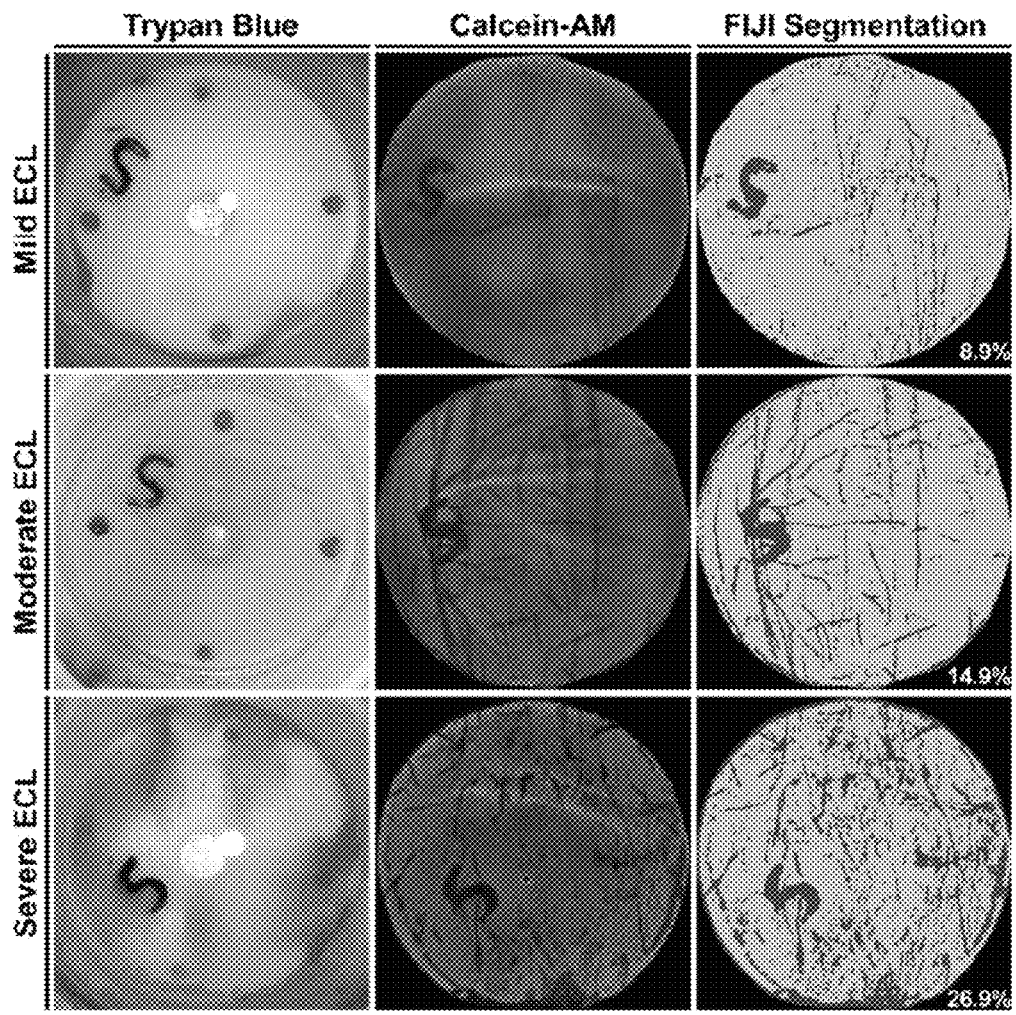

FIG. 9 is a series of images depicting patterns and example amounts of ECL on preloaded DMEK grafts. The panels at the left depict Trypan blue stained DMEK grafts just prior to loading. The middle panels depict Calcein-AM staining of DMEK grafts after removal from a corneal tissue carrier and opening of the DMEK grafts on a bed of viscoelastic. The panels at the right illustrate FIJI segmentation to quantify cell loss. Percent cell loss is shown in each of the panels at the right. The top right panel depicts an example of "mild" cell loss. The middle right panel depicts an example of "moderate" cell loss. The bottom right panel depicts an example of "severe" cell loss. The bottom edge of the DMEK graft depicted in the bottom right panel was heavily damaged due to incomplete trephination and increased manipulation during loading into a corneal tissue carrier.

Figure 10:
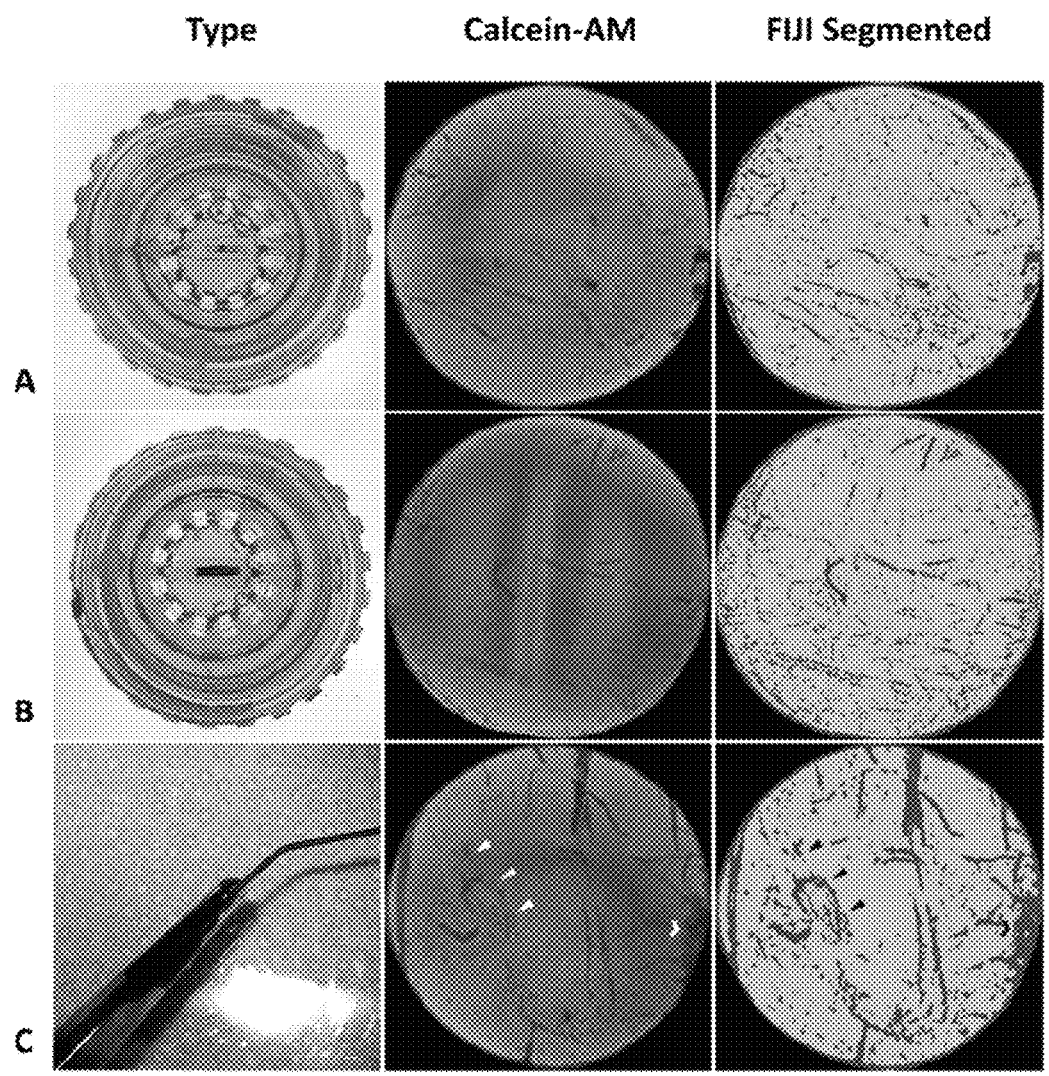

FIG. 10 is a series of images depicting ECL due to staining methods. The left column includes example images representing unstained preloaded grafts, prestained preloaded grafts, and preloaded grafts stained while inside of a Straiko modified Jones tube (injector). The middle column includes Calcein-AM stained images. The right column includes FIJI segmented images of the grafts in the middle column. Row A depicts an example of an unstained preloaded graft with 12.5% ECL. Row B depicts a prestained graft with 13.9% ECL. Row C depicts a preloaded graft stained inside of the injector with 20.6% ECL. Arrowheads show damage that may have been due to the graft scraping against the injector. The chevron indicates possible "contact" damage between graft and cannula.

Figure 11:
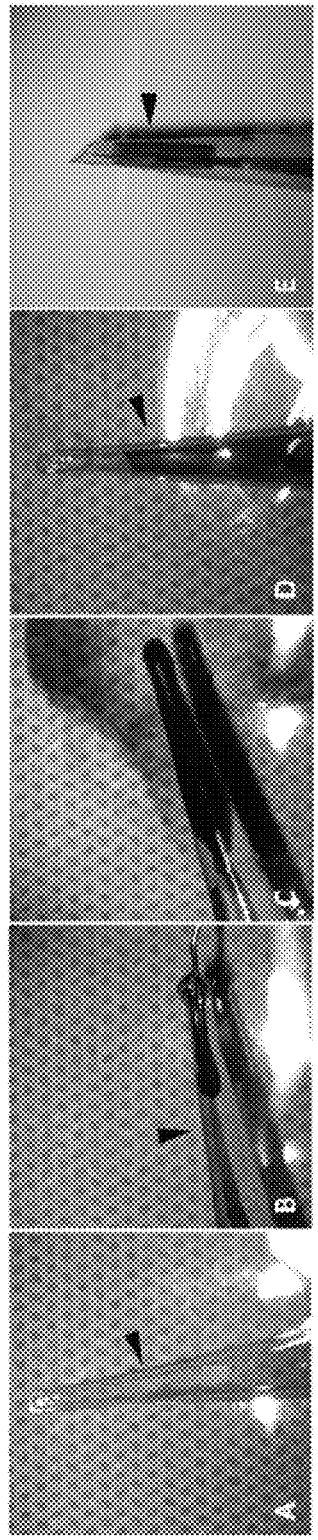

FIG. 11 is a series of images depicting staining of a DMEK graft inside of a modified Jones tube (injector). Black arrowheads show the location of the DMEK graft inside of the injector. Image A depicts that the unstained DMEK graft was positioned near the beveled opening of the injector. Image B depicts that a cannula was used to deliver Trypan blue for staining. Image C depicts that the graft was stained for 4 minutes. Image D depicts that balanced salt solution (BSS) was drawn into the injector to dilute the Trypan blue. Image E depicts the stained DMEK graft.

Figure 12A:
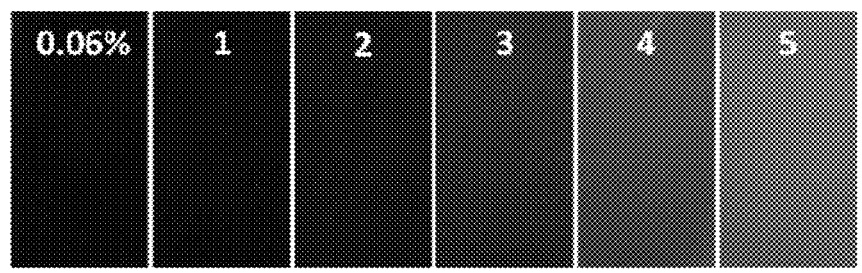

FIG. 12A is a series of images of Trypan blue serial dilution standards. The numbers represent dilutions from the original 0.06% Trypan blue concentration. Each dilution contains ½ of the Trypan blue concentration of the previous sample. The blue color of the Trypan blue is depicted in grayscale in the figures.

Figure 12B:
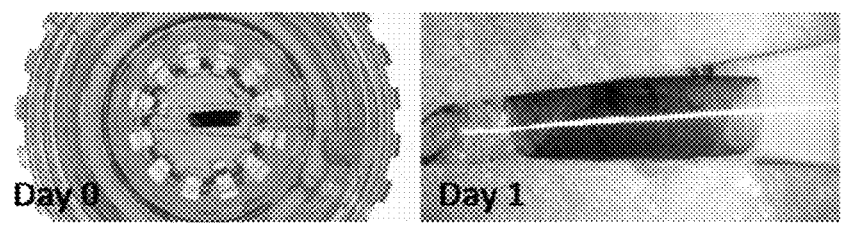

FIG. 12B is an image of a prestained graft before (Day 0) and an image of a prestained graft after overnight shipping (Day 1) from Oregon to New York.

Figure 12C:
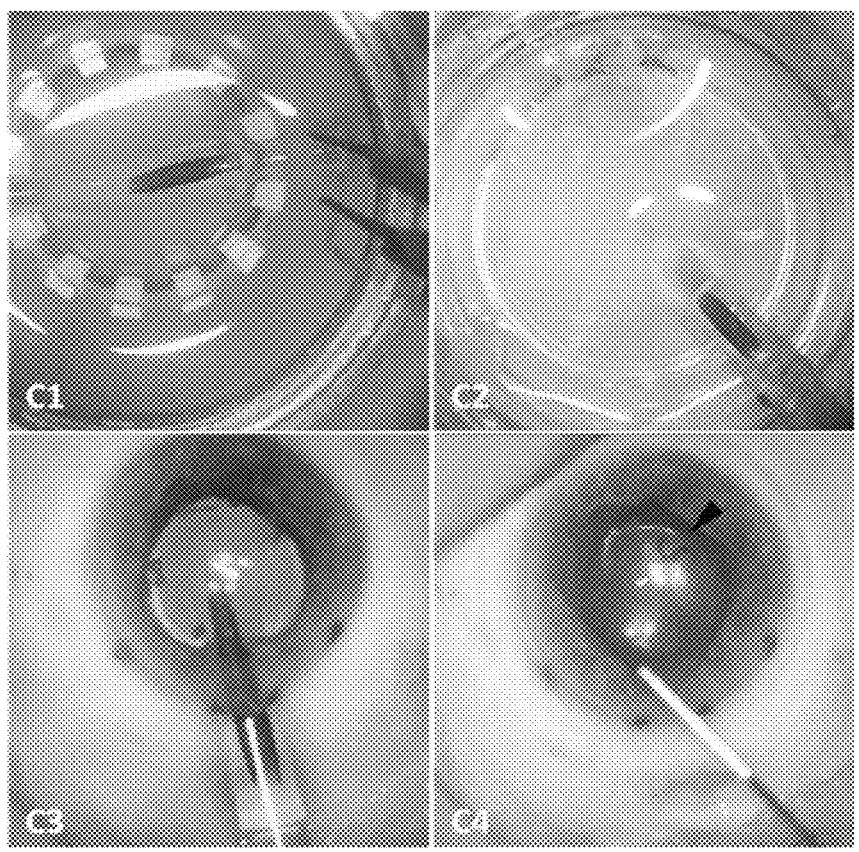

FIG. 12C is a series of still frames from a video showing a prestained graft being used in a simulated surgery after a 3-day shipping event. Image C1 depicts removal of the loaded injector from the viewing chamber. Image C2 depicts replacing the OPTISOL™-GS with BSS. Image C3 depicts delivery of the graft into the anterior chamber. Image C4 depicts that the graft was unscrolled and that the S-stamp was clearly visible and showed that the graft was in the proper orientation.

DETAILED DESCRIPTION

The various embodiments disclosed herein generally relate to assemblies for storing, handling, transporting, viewing, evaluating, and/or shipping corneal tissue. In some embodiments, the assemblies include a viewing chamber and a corneal tissue carrier. The assemblies may also include a corneal tissue sample, wherein the corneal tissue sample is disposed within the corneal tissue carrier. Also disclosed herein are methods of processing corneal tissue samples and methods of administering corneal tissue samples to a subject. The disclosed methods can include preparing and/or obtaining a corneal tissue sample assembly.

Various features of the corneal tissue sample assemblies disclosed herein may be grouped together in a single embodiment, figure, or description thereof for the purpose of streamlining the disclosure. Many of these features may be used alone and/or in combination with one another in the various embodiments.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the assembly is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component. The phrase "fluid communication" is used in its ordinary sense, and is broad enough to refer to arrangements in which a fluid (e.g., a gas or a liquid) can flow from one element to another element when the elements are in fluid communication with each other.

The term "resilient" refers to a component, device, or object having a particular shape that can then be elastically deformed into a different shape, but that may return to the original shape when unconstrained. For example, a resilient arm may extend from an inner surface of a viewing chamber and, in use, the resilient arm may then be constrained (i.e., temporarily engaged with a corneal tissue carrier) to elastically deform it into a second shape (i.e., displaced laterally due to interaction with the corneal tissue carrier), then unconstrained (i.e., removed from engagement with the corneal tissue carrier) such that the resilient arm returns to its first shape or substantially returns to its first shape.

Figure 1A:
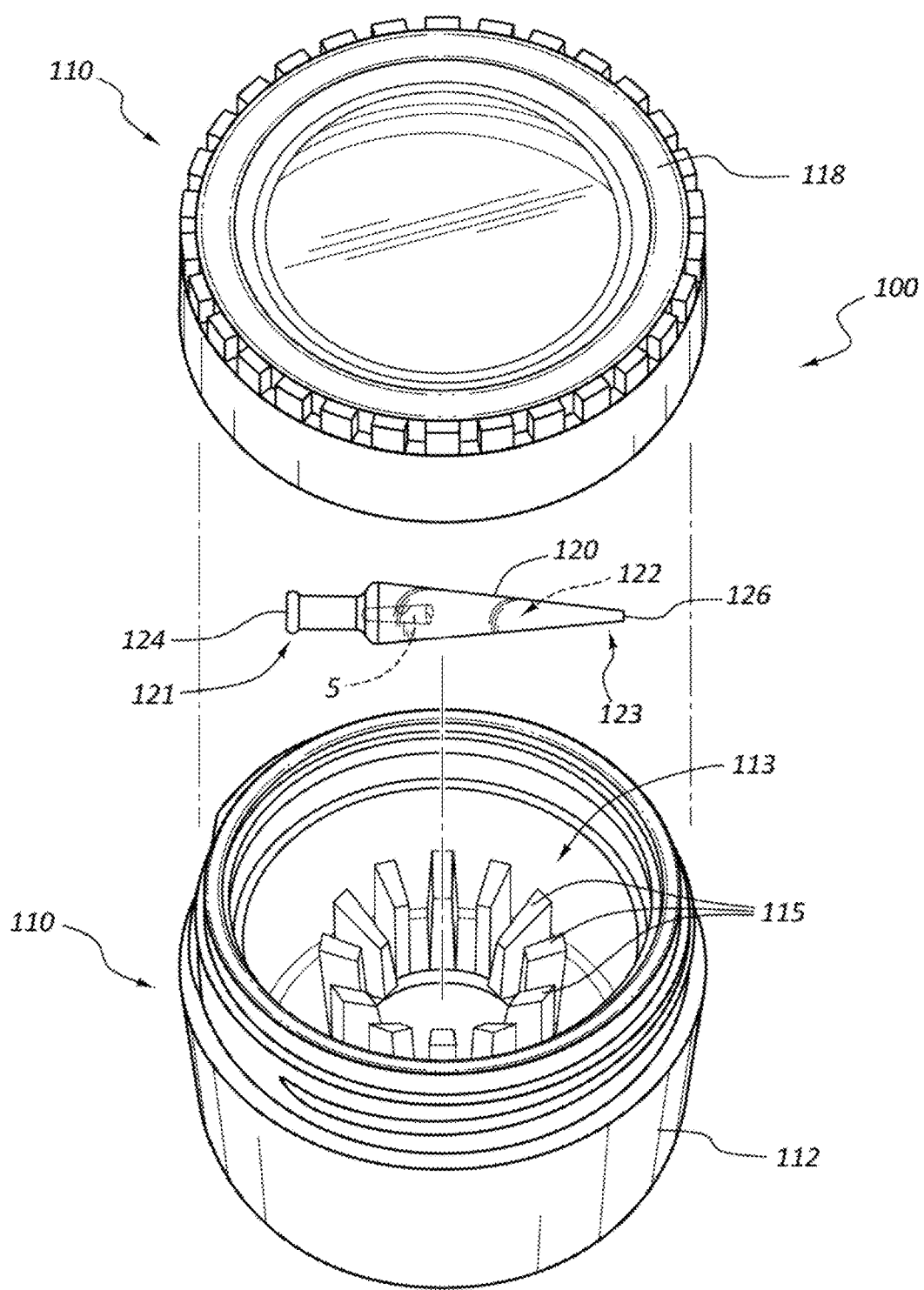
FIG. 1A is an exploded view of a corneal tissue sample assembly.
Figure 1B:
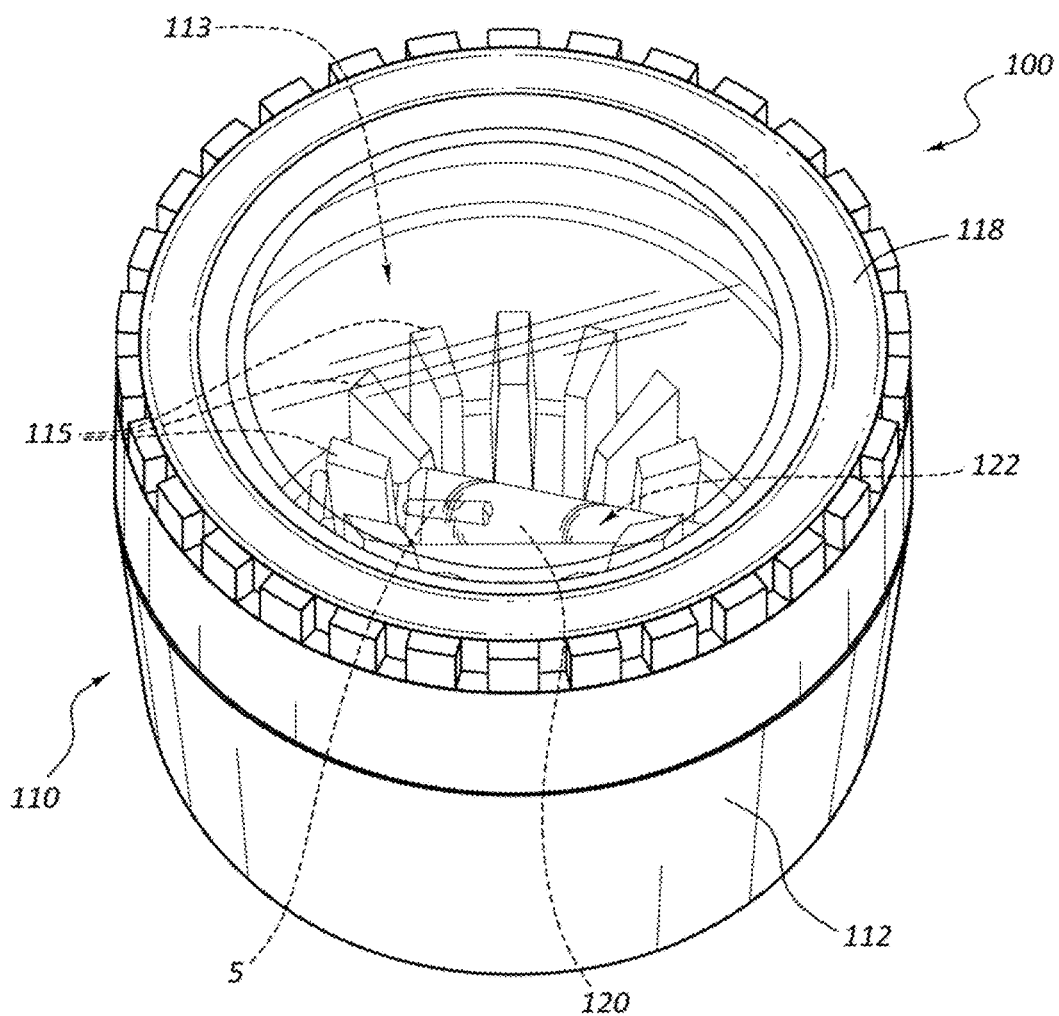
FIG. 1B is a perspective view of the corneal tissue sample assembly of FIG. 1A.
Figure 1C:
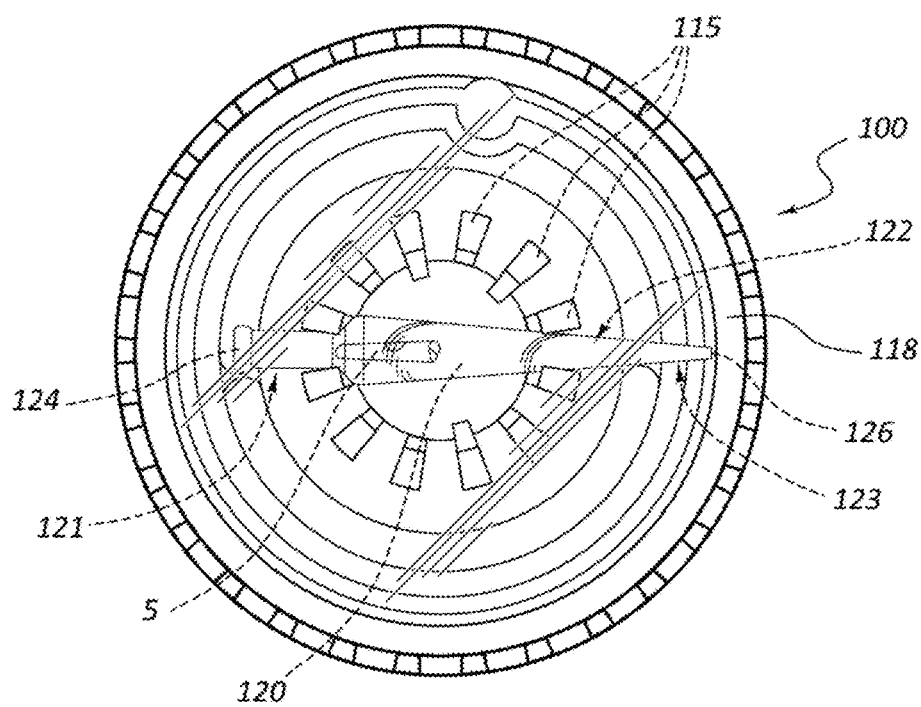
FIG. 1C is a top view of the corneal tissue sample assembly of FIG. 1A.
Figure 2:
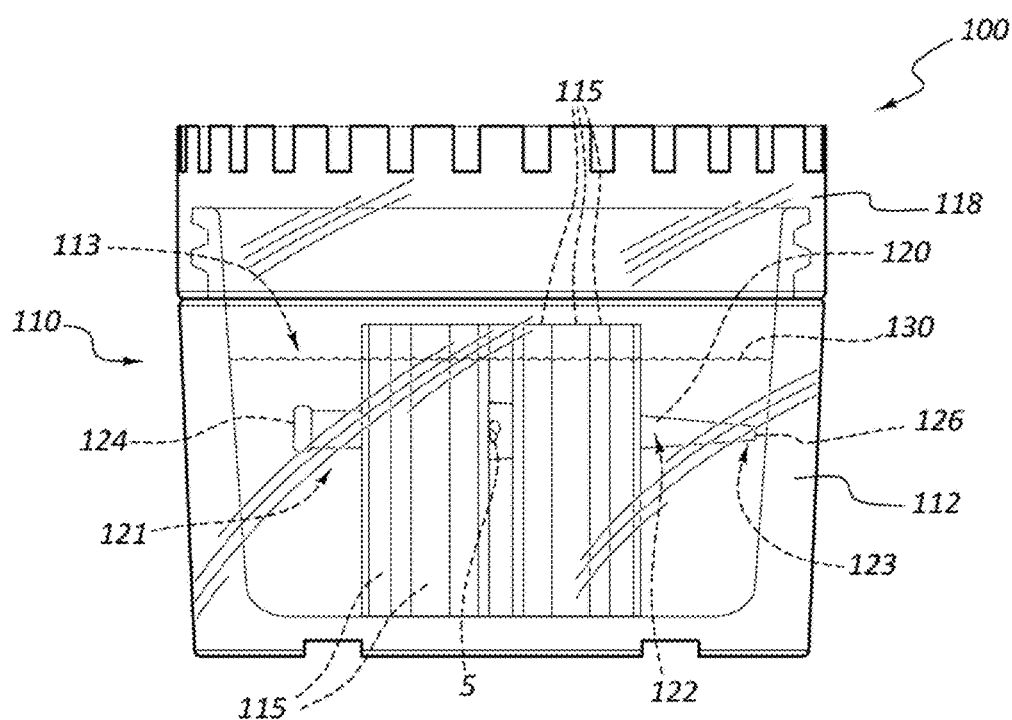
FIG. 2 is a side view of the corneal tissue sample assembly of FIGS. 1A-1C in a second configuration.

FIG. 1A is an exploded view of an assembly or corneal tissue sample assembly 100 for storing, handling, transporting, viewing, evaluating, and/or shipping corneal tissue. FIG. 1B is a perspective view of the assembly 100 in a closed configuration and FIG. 1C is a top view of the assembly 100. FIG. 2 is a side view of the assembly 100 in a second configuration. With reference to FIGS. 1A-2, the assembly can include a viewing chamber 110, wherein the viewing chamber 110 includes a body 112 and a lid 118. In some embodiments, the viewing chamber 110 may be a BAUSCH & LOMB™ corneal viewing chamber, a KROLMAN™ viewing chamber, a NUMEDIS INC.™ TRANSEND™ corneal tissue chamber, a STEPHENS INSTRUMENTS™ VISIONPAK™ disposable corneal viewing chamber, derivatives thereof, or another suitable viewing chamber. In various embodiments, the viewing chamber 110 may be formed from a polymer, a glass, or another suitable material. In specific embodiments, the viewing chamber 110 may be formed from a biocompatible material (e.g., a biocompatible polymer, a biocompatible glass, etc.).

The assembly 100 can further include a corneal tissue carrier 120 (also referred to herein as an injector, a Straiko modified Jones tube, a Jones tube, or a tube). The corneal tissue carrier 120 can be removably coupled to an inner portion 113 of the body 112 of the viewing chamber 110. In certain embodiments, the corneal tissue carrier 120 may be a Straiko modified Jones tube, a Jones tube, derivatives thereof, or another suitable tissue carrier. In some embodiments, the corneal tissue carrier 120 may be formed from a polymer, a glass, or another suitable material. In specific embodiments, the corneal tissue carrier 120 may be formed from a biocompatible material (e.g., a biocompatible polymer, a biocompatible glass, etc.).

When the corneal tissue carrier 120 is coupled to the inner portion 113 of the body 112, the lid 118 may be coupled to the body 112. In some embodiments, the lid 118 may not be in contact with the corneal tissue carrier 120 when the lid 118 is coupled to the body 112. In some other embodiments, the lid 118 may be in contact, or gently contact, the corneal tissue carrier 120 when the lid is coupled to the body 112.

The assembly 100 can further include a corneal tissue sample 5 (also referred to herein as a DMEK graft, a DMEK graft scroll, or a graft). The corneal tissue sample 5 may be suitable for various forms of keratoplasty or endothelial keratoplasty (e.g., DMEK, PDEK, DSAEK, Ultra-thin DSAEK, etc.). In some embodiments, the corneal tissue sample 5 may be a graft comprising corneal endothelium and Descemet membrane. In some other embodiments, the corneal tissue sample 5 may include corneal endothelium, Descemet membrane, and/or pre-Descemet's membrane. In particular embodiments, the corneal tissue sample 5 may be a DMEK graft or a graft suitable for a DMEK procedure. In alternative embodiments, the corneal tissue sample 5 may also include stroma. In certain embodiments, the thickness of the corneal tissue sample 5 may be less than about 200 microns, less than about 150 microns, less than about 100 microns, less than about 50 microns, less than about 25 microns, less than about 10 microns, or another suitable thickness. In particular embodiments, the thickness of the corneal tissue sample 5 is less than about 100 microns. In specific embodiments, the thickness of the corneal tissue sample 5 is less than about 50 microns. As shown, the corneal tissue sample 5 may be disposed within the corneal tissue carrier 120. In certain embodiments, the corneal tissue sample 5 may be stained before being disposed within the corneal tissue carrier 120. In certain other embodiments, the corneal tissue sample 5 may be disposed within the corneal tissue carrier 120 and then stained. For example, the corneal tissue sample 5 may be stained with Trypan blue, a mixture comprising Trypan blue, a biocompatible stain, or another suitable dye or stain.

In some embodiments, at least a portion of each of the viewing chamber 110 and the corneal tissue carrier 120 may be substantially transparent. The viewing chamber 110 and the corneal tissue carrier 120 may be substantially transparent such that the corneal tissue sample 5 can be visible to a user. For example, the corneal tissue sample 5 may be disposed within the corneal tissue carrier 120, and the corneal tissue carrier 120 including the corneal tissue sample 5 may be further disposed within the viewing chamber 110. In such configurations, the substantial transparency of the viewing chamber 110 and the corneal tissue carrier 120 may allow or permit the user to view the corneal tissue sample 5. In certain embodiments, the corneal tissue carrier 120 and the viewing chamber 110 are substantially transparent and/or substantially clear such that a user may view and/or evaluate the corneal tissue sample 5 disposed within the corneal tissue carrier 120 and the viewing chamber 110 using corneal tissue evaluation instruments and/or methods such as specular microscopy, slit-lamp biomicroscopy, light microscopy, and/or optical coherence tomography.

The corneal tissue carrier 120 can include an inner cavity 122, wherein the corneal tissue sample 5 can be disposed in the inner cavity 122. The corneal tissue carrier 120 can further include at least one opening or first opening 124. The first opening 124 may be disposed at or adjacent a first or proximal end 121 of the corneal tissue carrier 120. The corneal tissue carrier 120 can further include a second opening 126. The second opening 126 may be disposed at or adjacent a second or distal end 123 of the corneal tissue carrier 120. In some embodiments, the inner cavity 122 of the corneal tissue carrier 120 may be in communication (e.g., fluid communication) with the inner portion 113 of the body 112 of the viewing chamber 100 via the first opening 124 and/or the second opening 126.

The corneal tissue carrier 120 may have various sizes and/or shapes. For example, a length of the corneal tissue carrier 120 may be from about 10 mm to about 100 mm, about 25 mm to about 50 mm, about 30 mm to about 40 mm, or another suitable length. In some embodiments, the length of the corneal tissue carrier 120 may be about 32 mm, about 35 mm (e.g., about 35.2 mm), or about 38 mm (e.g., about 37.6 mm). A maximum width of the corneal tissue carrier 120 may be from about 1 mm to about 10 mm, from about 3 mm to about 8 mm, from about 5 mm to about 6 mm, or another suitable width. In some embodiments, the maximum width of the corneal tissue carrier 120 may be about 5.6 mm, about 5.9 mm (e.g., about 5.88 mm), or about 6 mm.

The first and second openings 124, 126 may also have various sizes and/or shapes. For example, the first and second openings 124, 146 may be substantially circular, substantially ellipsoidal, or another suitable shape. In some embodiments, the first opening 124 may be substantially circular, wherein the first opening 124 has an inside diameter and an outside diameter (i.e., the material forming the corneal tissue carrier 120 has a thickness). The outside diameter of the first opening 124 may be from about 2 mm to about 6 mm, about 3 mm to about 5 mm, about 3.5 mm to about 4 mm, or another suitable outside diameter. For example, the outside diameter of the first opening 124 may be about 3.8 mm, about 3.85 mm, or about 3.9 mm. The inside diameter of the first opening 124 may be from about 0.5 mm to about 4 mm, about 1 mm to about 3 mm, about 1.5 mm to about 2 mm, or another suitable inside diameter. For example, the inside diameter of the first opening 124 may be about 1.6 mm (e.g., about 1.64 mm), about 1.7 mm, or about 1.9 mm (e.g., about 1.87 mm).

In some embodiments, the second opening 126 may be substantially ellipsoidal, wherein the second opening 126 has an inside major axis, an outside major axis, an inside minor axis, and an outside minor axis. The outside major axis of the second opening 126 may be from about 1 mm to about 5 mm, about 1.5 mm to about 4 mm, about 2 mm to about 3.5 mm, or another suitable outside major axis. For example, the outside major axis of the second opening 126 may be about 2.2 mm (e.g., about 2.23 mm), about 2.7 mm (e.g., about 2.72 mm), or about 3 mm. The inside major axis of the second opening 126 may be from about 0.3 mm to about 4 mm, about 0.5 mm to about 3 mm, about 1 mm to about 2.5 mm, or another suitable inside major axis. For example, the inside major axis of the second opening 126 may be about 1.5 mm, about 1.9 mm (e.g., about 1.86 mm), or about 2.1 mm (e.g., about 2.14 mm).

Furthermore, the outside minor axis of the second opening 126 may be from about 0.5 mm to about 4 mm, about 1 mm to about 3 mm, about 1.5 mm to about 2.5 mm, or another suitable outside minor axis. For example, the outside minor axis of the second opening 126 may be about 1.9 mm (e.g., about 1.91 mm) or about 2.4 mm (e.g., about 2.38 mm). The inside minor axis of the second opening 126 may be from about 0.3 mm to about 4 mm, about 0.5 mm to about 3 mm, about 1 mm to about 2 mm, or another suitable inside minor axis. For example, the inside minor axis of the second opening 126 may be about 1.2 mm, about 1.4 mm (e.g., about 1.42 mm), or about 1.5 mm (e.g., about 1.52 mm).

In some embodiments, the corneal tissue carrier 120 may be configured to be coupled to a syringe, for example, the proximal end 121 of the corneal tissue carrier 120 may be coupleable to a distal end of a syringe (see FIG. 4). In certain embodiments, a portion of medical tubing may be coupled to the proximal end 121 of the corneal tissue carrier 120. The portion of medical tubing can be in fluid communication with the inner cavity 122 of the corneal tissue carrier 120 via the first opening 124. In certain embodiments, the medical tubing may be integral with the corneal tissue carrier 120. In certain other embodiments, each of the medical tubing and the corneal tissue carrier 120 may be discrete components.

With reference to FIG. 2, a preservation fluid 130 can be disposed within at least a portion of the inner portion 113 of the body 112 of the viewing chamber 110. Additionally, the preservation fluid 130 can be disposed within at least a portion of the inner cavity 122 of the corneal tissue carrier 120 (e.g., when the corneal tissue carrier 120 is disposed within the inner portion 113 of the body 112). In certain embodiments, the preservation fluid 130 may be disposed only within at least a portion of the inner cavity 122 of the corneal tissue carrier 120 and not within at least a portion of the inner portion 113 of the body 112 of the viewing chamber 110. In various embodiments, the preservation fluid 130 may be disposed within the inner portion 113 and the inner cavity 122 such that the corneal tissue sample 5 is substantially immersed in the preservation fluid 130. In certain embodiments, the preservation fluid 130 may be OPTISOL™-GS, OPTISOL™, LIFE4° C.™ (NUMEDIS™, Inc.), EUSOL-C™ (CORNEAL CHAMBER™, ALCHIMIA™, Sri), CORNEA COLD® (EUROBIO™), CORNISOL™ (AUROLAB™), a derivative thereof, or another suitable preservation fluid.

Referring again to FIGS. 1A-2, the body 112 of the viewing chamber 110 may include a plurality of arms or resilient arms 115 extending from an inner surface of the body 112 (e.g., an inner surface of the inner portion 113 of the body 112). The plurality of arms 115 may be configured to removably couple the corneal tissue carrier 120 to the inner portion 113 of the body 112. Each of the arms 115 may be resilient, such that each of the arms 115 has lateral flexibility. For example, in the illustrated embodiment the plurality of arms 115 are disposed in a circle (see FIG. 1C). Upon placement of the corneal tissue carrier 120 between at least two arms 115, each of the two arms 115 may be displaced substantially parallel with a tangent of the circle. The arms 115 can exert a force on the corneal tissue carrier 120 such that the corneal tissue carrier 120 is coupled to the body 112 of the viewing chamber 110 via the arms 115. For clarity, only a subset of the plurality of arms 115 is labeled in FIGS. 1A-2.

FIGS. 3A and 3B illustrate additional embodiments of corneal tissue carriers 220, 220' that can, in certain respects, resemble components of the corneal tissue carrier 120 described in connection with FIGS. 1A-2. It will be appreciated that all the illustrated embodiments may have analogous features. Accordingly, like features are designated with like reference numerals, with the leading digits incremented to "2." For instance, the inner cavity is designated as "122" in FIGS. 1A-2, and an analogous inner cavity is designated as "222" in FIG. 3A. Relevant disclosure set forth above regarding similarly identified features thus may not be repeated hereafter. Moreover, specific features of the corneal tissue carrier 120 and related components shown in FIGS. 1A-2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the corneal tissue carriers 220, 220' of FIGS. 3A and 3B. Any suitable combination of the features, and variations of the same, described with respect to the corneal tissue carrier 120 and components illustrated in FIGS. 1A-2 can be employed with the corneal tissue carriers 220, 220' and components of FIGS. 3A and 3B, and vice versa. This pattern of disclosure applies equally to further embodiments depicted in subsequent figures and described hereafter.

With reference to FIG. 3A, one or more caps or plugs 228a, 228b may be removably coupled to the corneal tissue carrier 220. A first cap 228a may be coupleable to a first end 221 of the corneal tissue carrier 220, for example, at or adjacent a first opening 224 of the corneal tissue carrier 220. In some other embodiments, a second cap 228b may be coupleable to a second end 223 of the corneal tissue carrier 220, for example, at or adjacent a second opening 226 of the corneal tissue carrier 220.

The caps 228a, 228b may inhibit or restrict passage of a corneal tissue sample out of the inner cavity 222 of the corneal tissue carrier 220. In some embodiments, the caps 228a, 228b may allow or permit passage of fluid (e.g., a preservation fluid) into and/or out of the inner cavity 222 of the corneal tissue carrier 220. As illustrated, one or more of the caps 228a, 228b may include at least one of a mesh material, a web-like material, and/or a permeable material. The cap (i.e., caps 228a, 228b) may include a mesh portion such that passage of a corneal tissue sample through the cap is substantially inhibited, while passage of a fluid through the cap is allowed or permitted. In some embodiments, a width of each of the openings in the mesh may be less than about 2 mm, less than about 1 mm, less than about 0.75 mm, less than about 0.5 mm, less than about 0.25 mm, less than about 0.1 mm, less than about 0.05 mm, less than about 0.02 mm, or another suitable size. In specific embodiments, a width of each of the openings in the mesh may be about 0.02 mm. In various embodiments, the caps 228a, 228b may include one or more apertures (e.g., openings).

With reference to FIG. 3B, one or more caps or plugs 228a', 228b' may be removably coupled to the corneal tissue carrier 220'. A first plug 228a' may be coupleable to a first end 221' of the corneal tissue carrier 220', for example, within at least a portion of a first opening 224' of the corneal tissue carrier 220'. A second cap 228b' may be coupleable to a second end 223' of the corneal tissue carrier 220', for example, at or adjacent a second opening 226' of the corneal tissue carrier 220'.

The caps or plugs 228a', 228b' may inhibit or restrict passage of a corneal tissue sample out of the inner cavity 222' of the corneal tissue carrier 220'. In some embodiments, the caps or plugs 228a', 228b' may inhibit or restrict passage of fluid into and/or out of the inner cavity 222' of the corneal tissue carrier 220' (e.g., the caps or plugs 228a', 228b' may seal, or substantially seal, the corneal tissue carrier 220'). Accordingly, a preservation fluid may be disposed only within at least a portion of the inner cavity 222' of the corneal tissue carrier 220' and not within at least a portion of an inner portion of a body of a viewing chamber. Any combination of caps or plugs (e.g., caps or plugs that allow passage of fluid and/or caps or plugs that inhibit passage of fluid) may be used with the corneal tissue carriers disclosed herein.

FIG. 4 depicts a corneal tissue carrier 320 coupled to a syringe 340. As shown, the corneal tissue carrier 320 may be coupled to the syringe 340 via a portion of medical tubing 345. In some embodiments, the medical tubing 345 may be about 14 French gauge. In some other embodiments, the medical tubing 345 may be about 6 French gauge, about 8 French gauge, about 10 French gauge, about 12 French gauge, about 16 French gauge, about 18 French gauge, about 20 French gauge, or another suitable size.

An assembly or corneal tissue sample assembly for storing, handling, transporting, viewing, evaluating, and/or shipping corneal tissue may lack a viewing chamber. In various embodiments, the assembly may include a corneal tissue carrier, one or more caps or plugs, and/or a syringe as depicted, for example, in FIGS. 3A-4. Furthermore, a corneal tissue sample may be disposed in the corneal tissue carrier. The corneal tissue sample may be immersed or substantially immersed in a preservation fluid that is disposed within at least a portion of the inner cavity of the corneal tissue carrier.

Methods related to processing a corneal tissue sample are also disclosed herein. In some embodiments, a method of processing a corneal tissue sample may include obtaining a corneal tissue sample and disposing the corneal tissue sample in an inner cavity of a corneal tissue carrier. As described above, the corneal tissue sample may be a graft comprising corneal endothelium and Descemet membrane. The corneal tissue sample may be suitable for various forms of keratoplasty (e.g., DMEK, PDEK, DSAEK, Ultra-thin DSAEK, etc.). In some embodiments, the corneal tissue sample may be a graft comprising corneal endothelium and Descemet membrane. In some other embodiments, the corneal tissue sample 5 may include corneal endothelium, Descemet membrane, and/or pre-Descemet's membrane. In particular embodiments, the corneal tissue sample is a DMEK graft or a graft suitable for a DMEK procedure. In specific embodiments, the corneal tissue sample may also include stroma. In some embodiments, the thickness of the corneal tissue sample may be less than about 200 microns, less than about 150 microns, less than about 100 microns, less than about 50 microns, less than about 25 microns, less than about 10 microns, or another suitable thickness. In particular embodiments, the thickness of the corneal tissue sample is less than about 100 microns. In specific embodiments, the thickness of the corneal tissue sample is less than about 50 microns. The method may also include staining the corneal tissue sample (e.g., with Trypan blue).

The method of processing the corneal tissue sample may further include coupling the corneal tissue carrier to an inner portion of a viewing chamber. As described above, the corneal tissue carrier may be coupleable to the inner portion of the viewing chamber via a plurality of arms extending from an inner surface of the viewing chamber.

Upon coupling of the corneal tissue carrier to the viewing chamber, the inner cavity of the corneal tissue carrier may be in fluid communication with the inner portion of the viewing chamber. In certain embodiments, the method of processing the corneal tissue sample may further include filling at least a portion of the inner portion of the viewing chamber and/or the inner cavity of the corneal tissue carrier with a preservation fluid such that the corneal tissue sample is substantially immersed in the preservation fluid. In certain other embodiments, the method of processing the corneal tissue sample may include filling at least a portion of the inner cavity of the corneal tissue carrier with the preservation fluid, while not filling the inner portion of the viewing chamber, and sealing the corneal tissue carrier (e.g., with caps or plugs) such that the corneal tissue sample is substantially immersed in the preservation fluid.

The method of processing the corneal tissue sample may also include closing or sealing the viewing chamber (e.g., with a lid) such that passage of the preservation fluid out of the inner portion of the viewing chamber is inhibited. In some embodiments, the viewing chamber may be tipped over (e.g., during transportation or shipping) and the lid may act to limit or prevent the leakage of the preservation fluid.

Upon disposition of the corneal tissue sample within the corneal tissue carrier and the viewing chamber, the corneal tissue sample may be viewed, assessed, and/or evaluated to determine the suitability of the corneal tissue sample for transplantation. In some embodiments, the corneal tissue sample, and any damage to the corneal tissue sample, can be evaluated to determine the suitability or the corneal tissue sample for transplantation. Damage to the corneal tissue sample can be "overall" damage (e.g., damage to any portion of the corneal tissue sample) or "concentrated" damage (e.g., damage that is concentrated at a certain portion or portions of the corneal tissue sample). Evaluating the corneal tissue sample may include using at least one of slit-lamp biomicroscopy, specular microscopy, light microscopy, and/or optical coherence tomography.

Figure 5A:
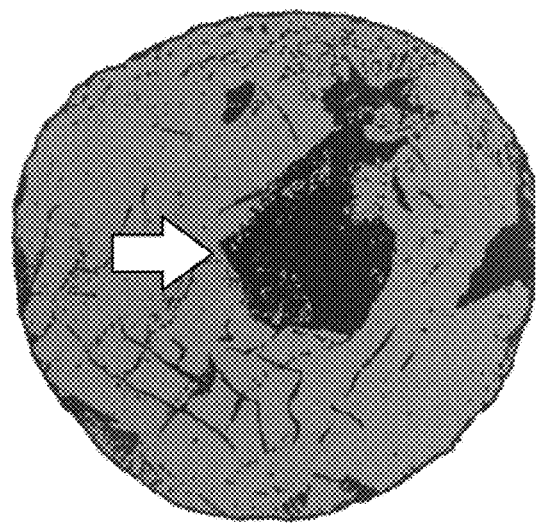
FIG. 5A is an image of a DMEK graft.
Figure 5B:
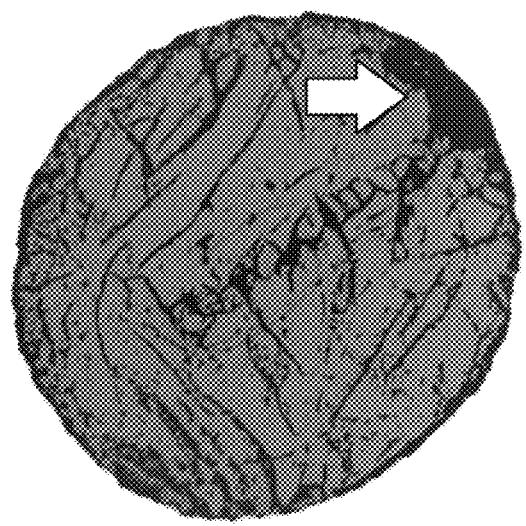
FIG. 5B is an image of another DMEK graft.

FIGS. 5A and 5B are images of DMEK grafts, wherein the dark areas are regions of endothelial cell death. In certain embodiments, a practitioner may determine that a corneal tissue sample is suitable for transplantation if the corneal tissue sample includes about 10% overall damage. In certain other embodiments, however, the practitioner may determine that a corneal tissue sample having about 10% damage is not suitable for transplantation if substantially all of the damage is concentrated at the center of the corneal tissue sample (e.g., as indicated by the arrow in FIG. 5A). Likewise, the practitioner may determine that a corneal tissue sample having about 10% damage is not suitable for transplantation if substantially all of the damage is concentrated along one edge of the corneal tissue sample (e.g., as indicated by the arrow in FIG. 5B). If damage is concentrated, for example, at the edge of the corneal tissue sample the corneal tissue sample may detach from a subject's eye after transplantation because there may be an insufficient number of cells along the edge of the corneal tissue sample.

In various embodiments, evaluating the corneal tissue sample may include at least one of assessing, calculating, counting, determining, and/or estimating an endothelial cell density (ECD) of the corneal tissue sample. A practitioner may reject the corneal tissue sample (e.g., determine the corneal tissue sample is not suitable for transplantation) when the ECD is below about 4000 cells/mm$^2$, below about 3000 cells/mm$^2$, below about 2500 cells/mm$^2$, below about 2000 cells/mm$^2$, below about 1500 cells/mm$^2$, below about 1000 cells/mm$^2$, or below another suitable number of cells/mm$^2$.

In certain embodiments, evaluating the corneal tissue sample may include at least one of assessing, calculating, counting, determining, and/or estimating a percentage of ECL of the corneal tissue sample. A practitioner may reject the corneal tissue sample when the estimated percentage of ECL is above about 5%, above about 10%, above about 15%, above about 20%, above about 25%, above about 30%, or above another suitable percentage.

In some embodiments, a practitioner may evaluate a corneal tissue sample and determine if the ECL is mild, mild-moderate, moderate, or severe (see, e.g., FIG. 9). The practitioner may determine that the corneal tissue sample is not suitable for transplantation if the ECL is severe. In various embodiments, 0% to about 10% ECL may be mild, about 10% to about 15% ECL may be mild-moderate, about 15% to about 20% ECL may be moderate, and above about 20% ECL may be severe.

The method of processing the corneal tissue sample may also include coupling a cap to an opening of the corneal tissue carrier. As discussed above, the cap may limit or inhibit passage of the corneal tissue sample out of the corneal tissue carrier. Furthermore, the cap may allow or permit passage of the preservation fluid into and out of the corneal tissue carrier.

Methods related to administering a corneal tissue sample to a subject in need thereof are also disclosed herein. In some embodiments, a method of administering a corneal tissue sample may include obtaining a corneal tissue sample assembly. The corneal tissue sample assembly, as described above, may include a viewing chamber, a corneal tissue carrier removably coupled to an inner portion of the viewing chamber, and a corneal tissue sample disposed within the corneal tissue carrier. A method of administering a corneal tissue sample may further include administering the corneal tissue sample to a subject. In some embodiments, the subject may be a patient in need of a corneal tissue transplant.

A method of administering a corneal tissue sample may include removing the corneal tissue carrier from the viewing chamber. In some embodiments, the corneal tissue sample may be a stained corneal tissue sample. In some other embodiments, the method of administering the corneal tissue sample may include staining the corneal tissue sample. The method of administering the corneal tissue sample may also include rinsing the stained corneal tissue sample. For example, the corneal tissue sample may be rinsed prior to administering the corneal tissue sample to the subject.

As stated above, the corneal tissue sample assembly may include a medical tubing that is coupled to the corneal tissue carrier. As such, a method of administering a corneal tissue sample may include coupling a syringe to the medical tubing and actuating the syringe to deliver the corneal tissue sample to the subject.

In some other embodiments, a method of administering a corneal tissue sample may include retrieving the corneal tissue sample from a corneal tissue carrier with a tool (e.g., a micro-forceps). The corneal tissue sample may then be pulled into the anterior chamber of the eye. This method of administering a corneal tissue sample may be referred to as the "pull-through" technique. In certain embodiments, the "pull-through" technique may be used with a corneal tissue sample (e.g., a DMEK scroll) disposed within a corneal tissue carrier as disclosed herein.

Figure 6:
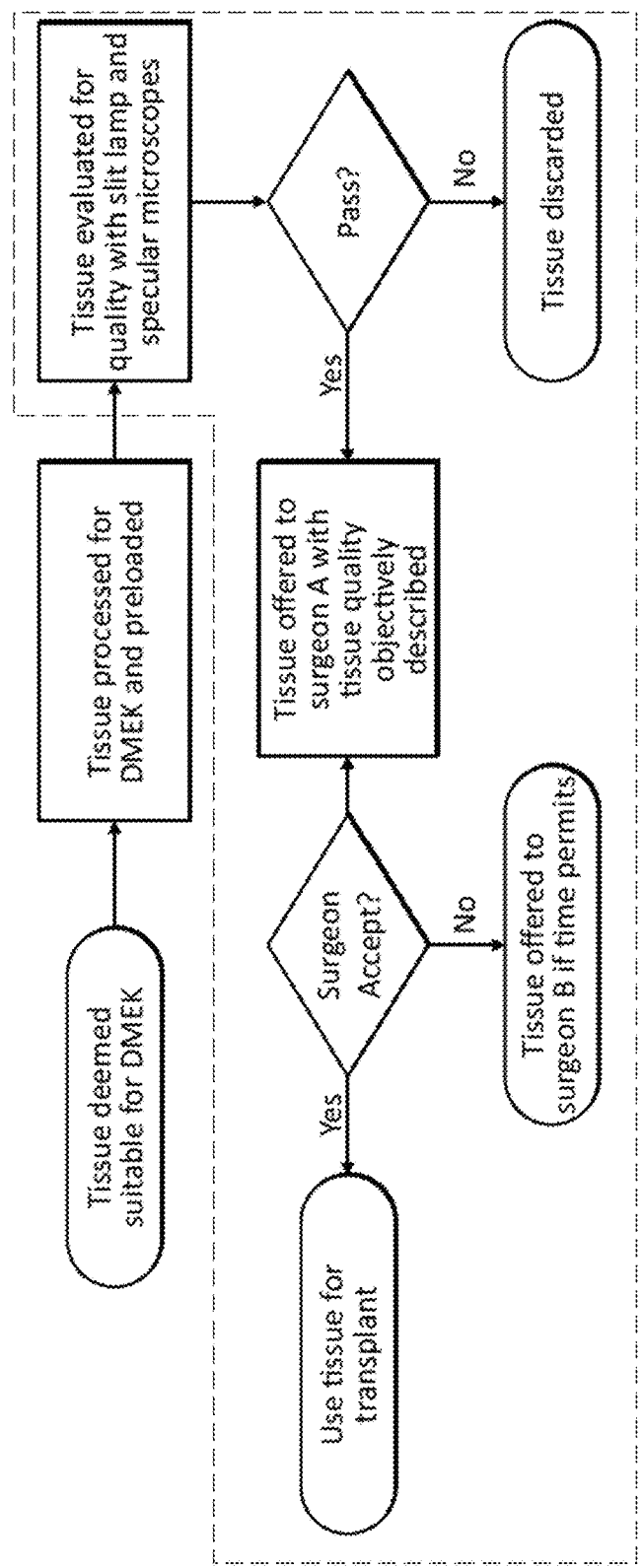
FIG. 6 is a flow chart depicting an embodiment of a method of processing, evaluating, and/or distributing a corneal tissue sample.

FIG. 6 is a flow chart illustrating a method of processing, evaluating, and/or distributing a corneal tissue sample ("tissue"). The flow chart also illustrates a method of providing information regarding a corneal tissue sample to a user (e.g., a surgeon). In some embodiments, the steps depicted within the dashed line may only be performed when the corneal tissue sample is disposed within a corneal tissue sample assembly as disclosed herein (i.e., wherein the corneal tissue sample is visible within the corneal tissue sample assembly). With continued reference to FIG. 6, a practitioner may determine that a corneal tissue sample is suitable for use in DMEK. Upon such a determination, the corneal tissue sample may be processed for DMEK and disposed within a corneal tissue assembly (i.e., the tissue may be "preloaded").

The suitability of the corneal tissue sample for transplantation (e.g., the "quality" of the corneal tissue sample) may be evaluated via slit-lamp biomicroscopy, specular microscopy, light microscopy, and/or optical coherence tomography. In certain embodiments, if the corneal tissue sample is determined to be unsuitable for transplantation it may not "pass" and the corneal tissue sample may be discarded. If, however, the corneal tissue sample is determined to be suitable for transplantation it may "pass" and the corneal tissue sample may be provided to a surgeon ("surgeon A") along with a description of the corneal tissue sample's quality.

Surgeon A may not accept the corneal tissue sample due to various factors (e.g., due to surgeon A's own preferences and/or requirements regarding a corneal tissue sample). In some embodiments, the rejected corneal tissue sample may be offered to another surgeon ("surgeon B"), if time permits. If, however, surgeon A accepts the corneal tissue sample, surgeon A may administer the corneal tissue sample to a subject (i.e., the corneal tissue sample may be transplanted). As can be appreciated, additional methods and/or method steps can be derived from FIGS. 1A-6 and the corresponding disclosure.

It has been demonstrated that good quality specular images of corneal tissue samples disposed within a corneal tissue carrier and a viewing chamber can be acquired, which can provide accurate ECD measurements (see, e.g., Study 1 described at least in part in Examples 1-12 below). In some embodiments, the number of cells that can be counted per image can be affected by the tightness of a DMEK graft scroll. For example, fewer cells can be counted on a graft that scrolls tightly (see FIG. 7C, top images), and these grafts may require up to four images to obtain the desired number of measured cells. Grafts that scroll loosely, however, can provide a flatter surface that can allow for more cells to be counted (see FIG. 7C, bottom images). These loosely scrolled grafts may require only three images to obtain ECD calculations based on >100 cells measured. In certain embodiments, post-processing cell counts may be measured.

In various embodiments, evaluation of the graft by slit-lamp biomicroscopy may be required for eye bank prepared tissues (see Eye Bank Association of America. 2016 *Medical Standards*. Washington D.C.: Eye Bank Association of America; 2016). In the processing validation round described herein, 16 preloaded grafts were prepared and loaded into the injectors. Technician-estimated tissue damage levels based on slit-lamp examination were lower than actual damage for 62% of grafts. This underestimation may have been due to further manipulation of the grafts prior to analysis. DMEK scrolls were injected into a bed of viscoelastic and unfurled for staining as previously reported (see Schallhorn J M, et al. *Cornea.* 2016; 35:377-382). Thus, the graft was once again pushed through the injector opening, possibly acquiring more damage, and then maneuvered to open by the injection of more viscoelastic. This technique of analysis, while necessary, has been shown to induce additional damage to DMEK grafts (see Schallhorn J M, et al. *Cornea.* 2016; 35:377-382).

Figure 7A:
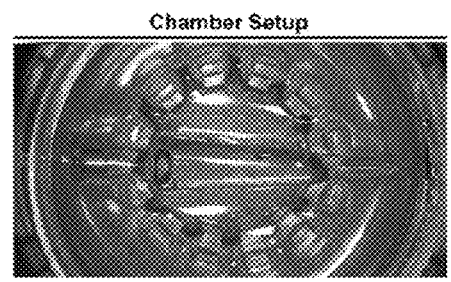
FIG. 7A is an image of a DMEK graft after disposition within a Straiko modified Jones tube (i.e., a preloaded DMEK graft) and further within a KROLMAN™ viewing chamber.
Figure 7B:
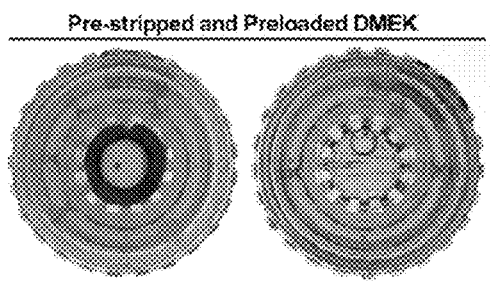
FIG. 7B is two images comparing an eye bank preparation of a pre-stripped DMEK graft attached to the stroma (left) and a preloaded DMEK graft disposed within a viewing chamber (right).

It was further found that estimation of graft damage improved over time. The largest differences between estimated ECL and actual ECL occurred in the first six grafts of the validation study (range: 4.4-15%), while the smallest differences were found in the last six grafts of the series (range: 0.9-7.1%) (see FIG. 7F). This trend continued for the grafts prepared for the shipping and extended viability studies. These results suggest that post-processing slit-lamp evaluations can be done with reasonable accuracy by trained eye bank technicians and evaluations may improve as technicians become more familiar with evaluating DMEK grafts in the scrolled conformation.

In some embodiments, a glass Straiko modified Jones tube may be used for post-processing evaluation. For example, a Jones tube can be useful in post-processing evaluation because it is substantially clear and it can fit into a KROLMAN™ viewing chamber. As many eye banks use KROLMAN™ viewing chambers, additional modifications to eye banks' procedures may not be required (see FIGS. 7A and 7B). Disposition of a Jones tube and a DMEK scroll inside of a viewing chamber can enable eye bank technicians to evaluate the grafts with equipment already on hand. In addition, surgeons and practitioners can continue to receive prepared tissues in a manner already familiar to them (see FIG. 7B).

Figure 8:
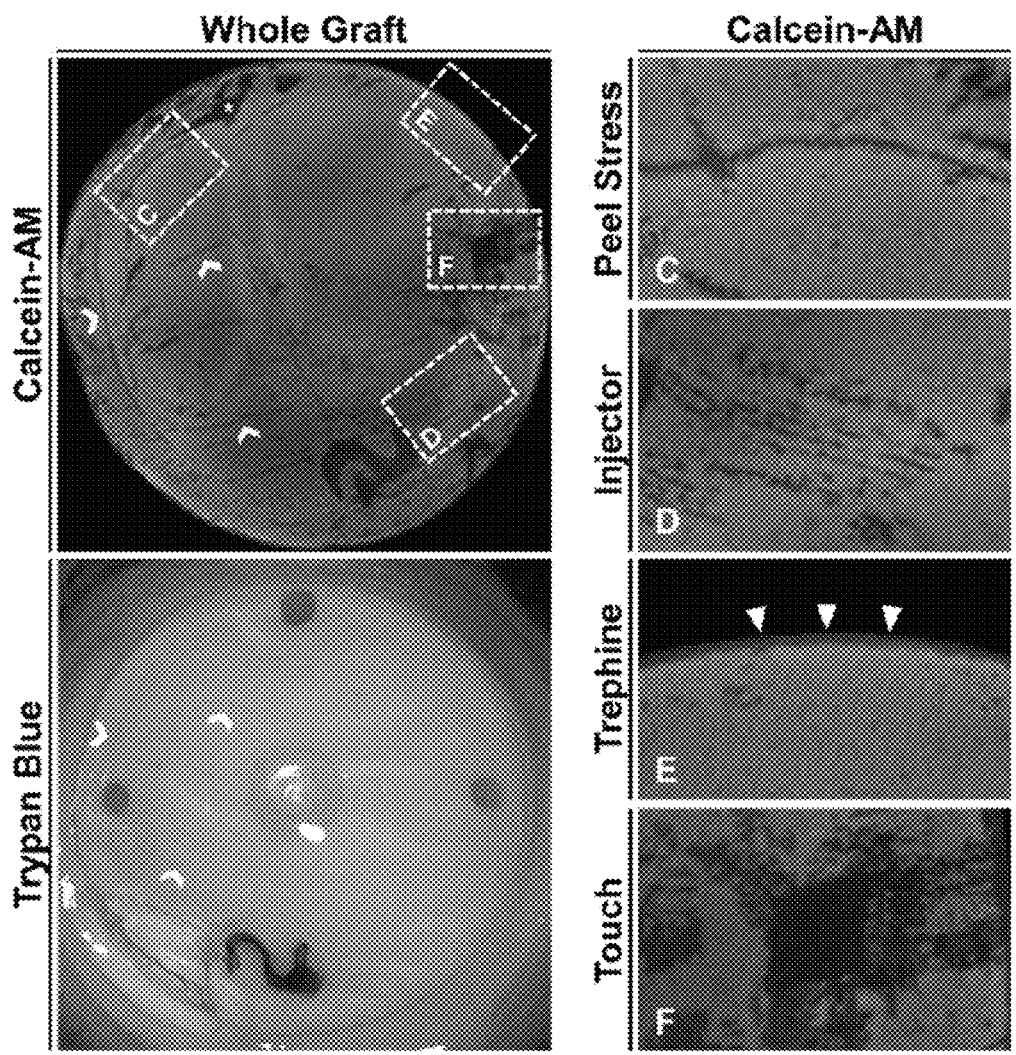
FIG. 8 is a series of images depicting examples of different types of DMEK graft damage. White chevrons in the images at the left indicate stress lines due to pre-stripping. White arrowheads in panel E indicate damage caused by trephine. Labeled regions in the image at the top left are enlarged in panels C-F as indicated. The image at the top left depicts a DMEK graft with examples of several types of damage stained with Calcein-AM. The asterisk (*)

At least one difference in the ECL of pre-stripped and preloaded grafts was observed in the studies disclosed herein (see Table 1). Pre-stripped tissues showed an average of 9.3±5.9% ECL (n=14), while preloaded grafts from the processing study showed an average ECL of 16.8±5.9% ECL (n=16), which was significantly higher than pre-stripped tissue alone. The difference in ECL may be due to the additional manipulation required to process preloaded tissues (e.g., graft trephination and loading into the injector) (see FIG. 8). Further, preloaded grafts are unfurled on a bed of viscoelastic for analysis, and therefore may be prone to additional damage caused by this analysis method. Similar to a previous study comparing ECL from two different injector systems (see Schallhorn J M, et al. *Cornea.* 2016; 35:377-382), the amount of ECL that includes trephination and injector damage may be more similar to ECL caused during actual surgical events. Thus, the ECL due to pre-stripping alone can be used as a baseline value for comparison of ECL added by preloading grafts.

TABLE 1

Endothelial Cell Loss (ECL) by Experimental Groups

|  | | ECL (% cell death) | | | Average ECD (cells/mm$^2$) | | | Donor Age (years) | | |
|---|---|---|---|---|---|---|---|---|---|---|
|  |  | Average ± | | | | | p- | | | |
|  | N | SD | Median | Range | Pre | Post | value | Average | Median | Range |
| Total Preloaded Tissues | 31 | 15.6 ± 6.4 | 14.1 | 6.9-50.4 | 2607 | 2724 | 0.1 | 64 | 65 | 46-75 |
| 1. Processing & Evaluation | 16 | 16.8 ± 5.9§ | 16.7 | 7.0-25.9 | 2528 | 2560 | 0.34 | 63 | 64 | 46-75+ |
| 2. Shipping Study | 10 | 18.5 ± 12.4 | 14.0 | 8.5-50.4‡ | 2697 | 2854 | 0.08 | 67 | 67 | 65-69 |
| 3. Extended Cell Viability | 5 | 13.1 ± 9.5 | 10.6 | 6.9-29.8† | 2634 | 2714 | 0.67 | 58 | 58 | 56-61 |
| Pre-stripped Only | 14 | 9.3 ± 5.9§ | 7.2 | 3.7-26.0* | 2701 | 2553 | 0.12 | 66 | 66 | 55-74+ |

The row labeled "Total Preloaded Tissues" contains combined results from the processing and evaluation, shipping, and extended cell viability studies.
P-values in the table are specific to pre- and post-processing ECD measurements.
§ECL is significantly different (p < 0.01).
+Age ranges not significantly different (p = 0.37).
‡One tissue fell out of the glass tube during a shipping event and incurred extensive damage.
†Tissue with 29.8% final ECL had approximately 17% ECL prior to processing based on Trypan blue staining and FIJI analysis.
*ECL pattern on graft with 26% damage suggests excess damage may have been caused during transfer of tissue to microscope slide for analysis.

In some embodiments, analysis of tissues processed earlier in the present study revealed higher than desired amounts of ECL (>25% ECL). The cell loss may have occurred due to several technical reasons, including partial trephination of the desired graft zone, scraping the graft against the opening of the injector while loading, and touch defects while unfurling the tissue for analysis (see FIGS. 8 and 9). However, improvement in graft quality was observed as the technicians continued to prepare additional grafts (see FIG. 7E). Improvements in graft quality were seen throughout the remainder of the study, as the median ECL decreased as technicians processed tissues for the shipping and extended cell viability experiments (see Table 1). Tissue quality may improve as trained eye bank technicians continue to prepare preloaded grafts.

Cell viability of grafts from the processing and evaluation study was not significantly different than cell viability of those grafts subjected to two shipping events (see Table 1). This may suggest that shipping preloaded grafts inside of a corneal tissue carrier and a viewing chamber does not cause additional graft damage.

An extended cell viability study was performed to examine whether preloaded DMEK grafts stored in OPTISOL™-GS can survive for several days in cold storage. The study was conducted to assess graft viability for surgeons who prefer to receive prepared grafts one day prior to scheduled surgeries as well as to account for possible shipping delays (e.g., due to weather). Thus, several grafts were prepared and stored in cold storage for five days prior to examining cell viability. With the exception of one graft that had 17% ECL prior to processing, all other grafts stored for five days showed ECL similar to those of the processing and shipping studies (see Table 1). Thus, preloaded grafts can survive in cold storage for an extended period of time.

In a second study of prestained and preloaded DMEK grafts, average donor age was 58 years (range: 50-75 years), 10% were pseudophakic, and 10% had a history of diabetes (see, e.g., Study 2 described at least in part in Examples 13-16 below). Endothelial cell densities for tissues used in studies where ECL was measured ranged from 2066-2994 cells/mm$^2$ (average: 2560 cell/mm$^2$).

Unstained preloaded DMEK grafts that were stored for 3 days in cold storage showed an average of 15±3% cell loss (95% CI=11-18%, n=5), and was not significantly different from prestained grafts, which had an average cell loss of 16±4% (95% CI=10-22%, n=5, P=1.0) (see FIG. 10). Grafts that were preloaded and then stained inside the injector showed an average of 18±2% cell loss (95% CI=16-20%, n=5), and was not significantly different than grafts that were prestained (P=0.15) or unstained (P=0.09) (see FIG. 10, row C and FIG. 11).

All 8 prestained grafts remained contained by the glass injector after being shipped from Portland, Oreg. to New York City, N.Y. Two grafts settled at the beveled tip of the modified Jones tube and 3 grafts settled in the flanged base of the tube. In all cases, less than 1 mm of the scroll extended beyond the edge of the glass tube. The grafts were repositioned into the center of the Straiko modified Jones tube by holding the viewing chamber such that the tube was oriented vertically and gently agitating the chamber. Two of the preloaded Straiko modified Jones tubes arrived with small air bubbles in the tube. While still submerged in OPTI-SOL™-GS and cradled in the viewing chamber, the air bubbles were exchanged for OPTISOL™-GS using a 30-gauge cannula.

Prior to shipping, all grafts were stained deep blue to levels between the 1$^{st}$ and 2$^{nd}$ dilutions (see FIG. 12A, panels 1 and 2). As stated above, the blue color of the Trypan blue is depicted in grayscale in the figures. One day post-processing and after cross-country shipment, the grafts remained blue with levels between the 3$^{rd}$ and 4$^{th}$ dilutions (n=3, see FIG. 12B, panels 3 and 4). Grafts examined 3 days after processing and cross-country shipment appeared lighter with blue levels between the 4$^{th}$ and 5$^{th}$ dilutions (n=5, see FIG. 12C, panels 4 and 5). Despite a reduction in stain levels, all grafts prepared 3 days prior to simulated surgery were visible after injection into donor eyes and were opened successfully (see FIG. 12C).

It was shown that preloaded DMEK tissues can be prestained with Trypan blue for 4 minutes and stored in cold storage for up to 3 days without a significant increase in cell loss compared to unstained tissues. These results were consistent with a recent report showing that staining DMEK grafts with 0.06% Trypan blue for up to 5 minutes yielded sufficiently blue grafts without additional cell loss (see Majmudar P A, et al. Enhancing DMEK Success by Identifying Optimal Levels of Trypan Blue Dye Application to Donor Corneal Tissue. *Cornea*. 2016). Furthermore surgeons have stained DMEK grafts with 0.06% Trypan blue for 4 minutes prior to transplantation without negatively affecting surgical outcomes (see Terry M A, et al. Cornea. 2015; 34:845-852).

Previous studies have demonstrated different methods used to preload DMEK grafts at the eye bank (see Parekh M, et al. *Am J Ophthalmol*. 2016; 166:120-125 and Tran K D, et al. *Cornea*. 2017; 36:484-490), and one study has shown that grafts can be evaluated accurately after loading into the Straiko modified Jones tube (see Tran K D, et al. *Cornea*. 2017; 36:484-490). While the purpose of this study was not to examine whether prestained tissue can be evaluated according to current standards (see Eye Bank Association of America. 2016 *Medical Standards*. Washington D.C.: Eye Bank Association of America; 2016), it was found that both specular microscopy and slit-lamp examination were possible with prestained preloaded tissues. For prestained grafts, all external surfaces of the scroll can be evaluated by rotating the chamber during slit-lamp evaluations. However, it can be difficult to visualize the endothelium that is on the interior of a tightly scrolled prestained graft as the scroll is less transparent due to staining. In these instances, visualization can be aided by retro-illumination of the scrolled graft by shining a light source (e.g., a pen light) through the graft towards the observer.

A protocol for staining DMEK grafts once they are loaded in the modified Jones tube was also examined (see FIG. 11). While a significant increase in ECL was not seen in this protocol, a trend towards additional cell loss was seen. Without being bound by any one particular theory, a larger sample size may reveal a small but significant increase in ECL that would be consistent with additional tissue manipulation resulting from the staining and washing steps. Damage patterns such as the fine scratch-like streaks observed on these grafts (see FIG. 10, row C) may be due to additional scraping against the injector as previously suggested (see Schallhorn J M, et al. *Cornea*. 2016; 35:377-382). Indeed, a review of videos from Study 2 shows where the scraping damage may have been introduced.

In the shipping studies, a subset of prestained grafts 3 days post-processing were chosen to be examined to push the limits of stain retention. It has been shown that prestained grafts retain a sufficient level of darkness after a 3-day shipping period (see FIGS. 12A-12C). However, it was noted that there was a noticeable reduction in the level of staining on the grafts analyzed in this study. Thus, prestained DMEK grafts do not retain 100% of the stain intensity when stored in OPTISOL™-GS for several days. This may also increase the difficulty of graft visualization and unscrolling during transplants for surgeons who are just starting to learn DMEK.

As demonstrated, pre-stripped and pre-punched DMEK grafts can also be prestained and preloaded into a clinical injector with acceptable cell loss. In addition, it has been shown that these highly processed tissues retain a sufficient level of stain for implantation and unscrolling after shipment to a distant surgical center.

EXAMPLES

The following examples are illustrative of disclosed methods and assemblies. In light of this disclosure, those of skill in the art will recognize that variations of these examples and other examples of the disclosed methods and assemblies would be possible without undue experimentation.

Example 1—Preloaded DMEK Grafts in Viewing Chambers

Examples 1-12 describe a first study (Study 1). After separation from the underlying stroma, all DMEK grafts (31/31) submerged in OPTISOL™-GS scrolled into their natural conformations with the endothelium facing outward. Grafts remained in the scrolled conformation after being drawn into a Straiko modified Jones tube (see FIG. 7A). The tube containing the graft was placed into a KROLMAN™ viewing chamber between the cornea support prongs or arms (see FIG. 7A). The chamber was filled with 20 mL of OPTISOL™-GS and then sealed by replacement of the lid. As a result, the presentation of the preloaded graft inside the viewing chamber was similar to current tissue presentation after preparation at the LIONS VISIONGIFT™ eye bank (see FIG. 7B).

Example 2—Specular Microscopy of Preloaded DMEK Grafts

Figure 7C:
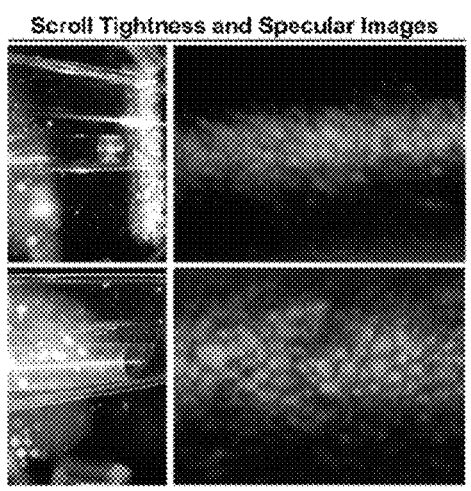
FIG. 7C is a series of images of preloaded DMEK grafts. Scroll tightness of preloaded DMEK grafts can be seen in slit-lamp biomicroscopy images (left). A specular microscopy image of a "tight" DMEK graft scroll is depicted at the top right and a specular microscopy image of a "loose" DMEK graft scroll is depicted at the bottom right.

Specular images and ECDs of all preloaded grafts used in this study were successfully obtained (31/31 grafts; see FIG. 7C). Average ECD for all tissues prior to processing was 2607±312 cells/mm$^2$, and was not significantly different from the post-processing average of 2724±339 cells/mm$^2$ (p=0.10; see Table 1). The average number of cells used to calculate ECD for preloaded grafts was 97±17 cells, and ranged from 71-130 cells. The number of cells that can be measured was determined by scroll tightness, with looser scrolls allowing for more cells to be counted (see FIG. 7C).

Example 3—Slit-Lamp Biomicroscopy and Cell Viability of Preloaded DMEK Grafts

Figure 7D:
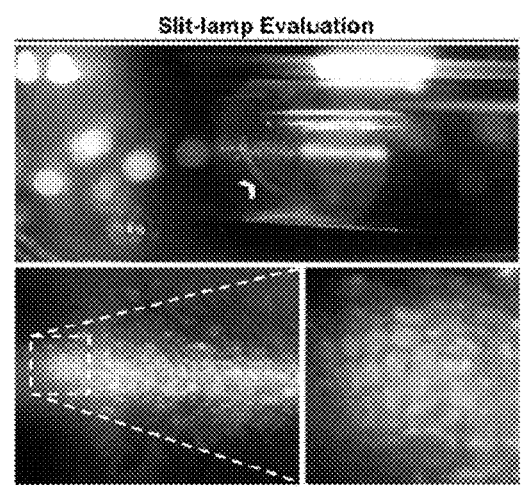
FIG. 7D is a series of slit-lamp biomicroscopy images of a preloaded DMEK graft. Examples of a stress line (top, yellow chevron) and a specular reflection (bottom left) are depicted. An enlarged image of the outlined area in the image at the bottom left is depicted at the bottom right.
Figure 7E:
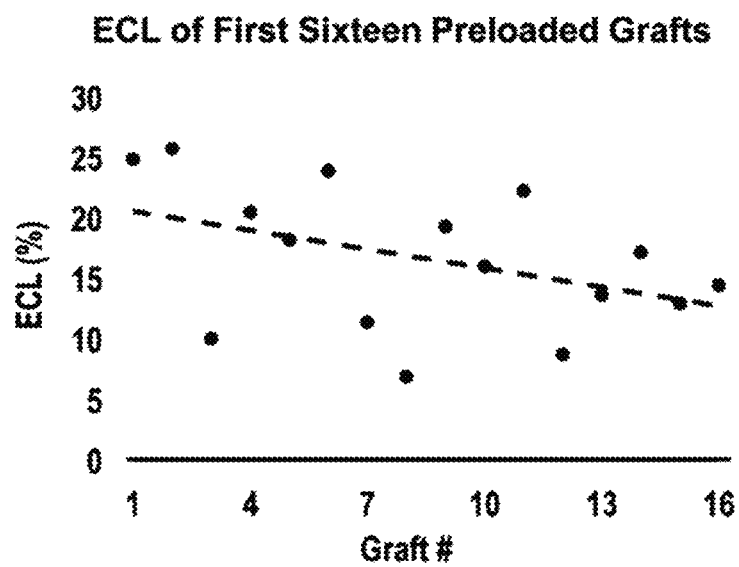
FIG. 7E is a scatter plot and trend line of endothelial cell loss (ECL) for the 16 DMEK grafts used in a processing and evaluation study (depicted in chronological order).
Figure 7F:
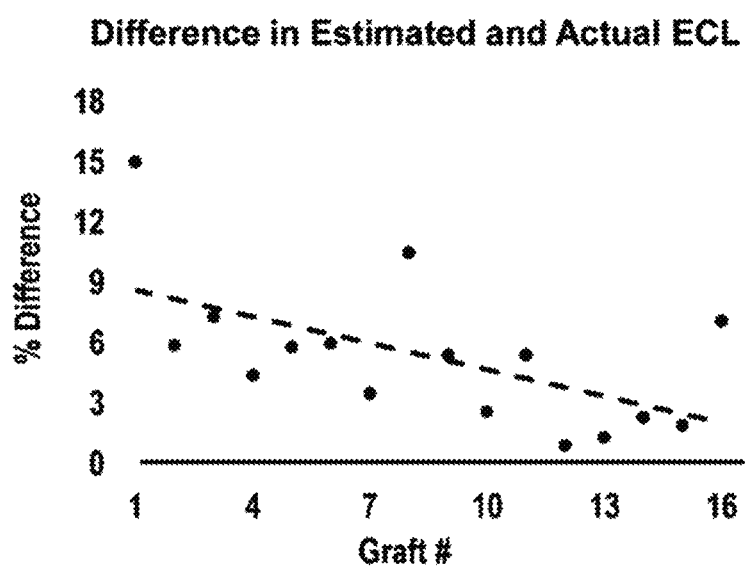
FIG. 7F is a scatter plot and trend line of the difference in estimated and actual ECL for the 16 DMEK grafts depicted in FIG. 7E.

To determine whether preloaded grafts can be sufficiently evaluated by slit-lamp biomicroscopy, a validation study was performed to determine how well technicians can identify ECL due to the preparation process. Sixteen preloaded grafts were prepared by three trained eye bank technicians and each graft was evaluated using the slit lamp by a technician who did not prepare that graft (see FIG. 7D). Various patterns of graft damage due to pre-stripping, injector loading/unloading, and touch defects were observed during slit-lamp evaluation and revealed by Calcein-AM staining (see FIG. 8). However, no specific defects caused by the tissue settling on the glass tube were observed.

Overall, the average estimate ECL for all grafts was 15.6±5.8% (range: 7.5-30.0%). Quantified ECL by vital-dye staining and analysis using FIJI Weka Segmentation revealed an average ECL of 16.8±5.9% (range: 7.0-25.9%). Total ECL of preloaded grafts was underestimated 62% of the time, and the average difference between estimated and actual ECL was 5.3±3.6% (range: 0.9-15%). The amount of quantified ECL, and the differences in estimated and actual ECL, decreased over the course of this study (see FIGS. 7E and 7F).

Example 4—ECL Due to Eye Bank Pre-Peeling Alone

To examine whether there is a difference in ECL between the preparation of preloaded DMEK grafts and the current eye bank prepared DMEK grafts (pre-stripping alone), 14 DMEK grafts were prepared under the current protocol of the LIONS VISIONGIFT™ eye bank and ECL was analyzed using vital-dye staining and FIJI. The average ECL due to peeling alone was 9.3±5.9% (median: 7.2%, range: 3.7-26.0%) and was significantly lower than that of preloaded tissues (p<0.01; see Table 1). Donor age range and pre-processing ECD measurements for these grafts were not significantly different than the 16 preloaded grafts examined above (p=0.37 and p=0.19, respectively). Therefore, the preloaded grafts prepared in this study showed a higher amount of ECL than tissues subjected to pre-stripping alone.

Example 5—Shipping of Preloaded DMEK Grafts

To test whether it is feasible to ship preloaded grafts in the present setup, and to examine whether shipping events induce additional damage to the grafts, shipping studies were performed using 10 preloaded grafts over three shipments. Each shipment contained two shipping events where tissues were shipped from the LIONS VISIONGIFT™ eye bank to the University of Texas Southwestern Medical Center at Dallas Transplant Services Center (UT-Southwestern) and back to the LIONS VISIONGIFT™ eye bank for analysis (~48 hours from preparation to analysis). Of the 10 tissues shipped, only one fell out of the Straiko modified Jones tube and settled on the bottom of the viewing chamber, which constituted a 90% success rate for this series of shipping events. The average amount of ECL of the 10 shipped tissues was 18.5±12.4% (median: 14.0%, range 8.5-50.4%), and this included the tissue that fell out of the Jones tube which incurred 50.4% ECL. When the graft that was dislodged from the carrier tube is excluded, the average ECL from this shipping study decreased to 15.0±5.7% (median: 13.5%, range: 8.5-26.4%), and was not significantly different than preloaded tissues that were not shipped (p=0.48). These results indicate that preloaded DMEK grafts can be shipped with minimal additional damage if they remain within the glass carrier tube.

Example 6—Extended Viability of Preloaded DMEK Grafts

To test the extended viability of preloaded DMEK grafts, five preloaded tissues were prepared and stored at 4° C. for five days prior to analysis by vital-dye staining and FIJI. Average ECL at the end of the five-day study was 13.1±9.5% (median: 10.6%, range: 6.9-29.8%). One tissue showed 29.8% ECL after five days in storage; however, Trypan blue staining of this tissue prior to processing revealed approximately 17% cell death. Thus, the increase in cell loss due to processing and long-term storage (~12.8%) was within the range of the other four tissues analyzed in this arm of the study. Taken together, these results suggest that preloaded tissues can survive for at least five days post preparation when placed in a viewing chamber filled with 20 mL of OPTISOL™-GS.

Example 7—Donor Characteristics

A total of 45 research corneas suitable for DMEK were utilized. Donor age range was 46-75 years (median of 65 years), 51% were male, 9% were pseudophakic, and 20% had a history of diabetes. Death to recovery time for all tissues was between 3 and 24 hours. ECD ranged from 1751 cells/mm$^2$ to 3,125 cells/mm$^2$ (median of 2,660 cells/mm$^2$). Donor age range and average ECD for specific experiments are summarized in Table 1.

Example 8—Tissue Preparation

All donor corneas used in this study were deemed unsuitable for transplant due to reasons other than endothelial pathology. Pre-stripped DMEK grafts were prepared according to previously described protocols (see Holiman J, et al. In: Mohit Parekh.; Stefano Ferrari D P, ed. *Eye Banking:*

Nova Biomedical; 2015:123-139 and Veldman P B, et al. *Cornea.* 2015) by trained eye bank technicians at the LIONS VISIONGIFT™ eye bank (Portland, Oreg., USA) who routinely prepare grafts for transplant use. Preloaded DMEK graft preparations are described in greater detail below. All prepared grafts were stored at 4° C. in 20 mL of OPTI-SOL™-GS after preparation (BAUSCH & LOMB™, St. Louis, Mo., USA).

Pre-processing and post-processing evaluation were performed according to the standard operation procedures of LIONS VISIONGIFT™ and EBAA Medical Standards (see Eye Bank Association of America. 2016 *Medical Standards.* Washington D.C.: Eye Bank Association of America; 2016). Slit-lamp images were acquired on a HAAG-STREIT™ BX 900® slit-lamp system (HAAG-STREIT™ USA, Mason, Ohio, USA) equipped with a CANON™ digital SLR camera (CANON™ USA, Melville, N.Y., USA), and specular images were acquired on a KONAN™ KERATO ANA-LYZER EKA-10™ with the EB10 software package (KO-NAN™ MEDICAL, Irvine, Calif., USA). For standard pre-peeled DMEK grafts, three central images were acquired and approximately 100 cells were used to determine ECD (at least 50 cells were counted per image). For preloaded grafts, three to four images were acquired centrally and an average of 97 cells were measured to calculate ECD.

Example 9—Preloading DMEK Grafts

After the application of an S-stamp, grafts were laid flat onto the underlying stroma. An 8.0 mm Hessburg-Barron trephine (BARRON PRECISION INSTRUMENTS™, Grand Blanc, Mich., USA) was used to excise the graft. Excess endothelium-Descemet membrane surrounding the graft zone was removed. Grafts were stained with Trypan blue (U-BLUE™; USIOL™, Lexington, Ky., USA) for 30 seconds and washed gently with BSS PLUS® irrigating solution (ALCON®, Ft. Worth, Tex., USA). Images of the Trypan blue stained grafts were imaged using a ZEISS™ OPMIMD S-5 microscope (ZEISS™, Thornwood, N.Y., USA) equipped with an OPTRONICS® MICROCAST® HD digital camera (OPTRONICS®, Goleta, Calif., USA) to document cell loss pattern due to pre-stripping. Grafts were submerged in OPTISOL™-GS, lifted using a MORIA™ micro-dissector (MORIA™, Antony, France), and allowed to scroll for two minutes.

Loading of the injector was performed with minor modifications to a previously described technique (see Terry M A, et al. *Cornea.* 2015; 34:845-852). In brief, a Straiko modified Jones tube (GUNTHER WEISS SCIENTIFIC GLASS-BLOWING™, Portland, Oreg., USA) was prepared by attaching approximately 15 mm of #14 French naso-gastric catheter tubing to the base of the Jones tube (COVIDIEN™, Mansfield, Mass., USA). The other end of the catheter tubing was attached to a 5 mL syringe, and the whole injector apparatus was filled with OPTISOL™-GS. DMEK scrolls were drawn into the injector, and the Jones tube was removed from the catheter tubing and syringe. The Jones tube containing the scrolled graft was placed inside a KROLMAN™ viewing chamber (KROLMAN™, Boston, Mass., USA).

Example 10—Shipping of Preloaded DMEK Grafts

A total of 10 preloaded DMEK grafts were shipped over three separate occasions during the course of one month. On each occasion, tissues were packed using standard eye bank protocol and shipped overnight from the LIONS VISION-GIFT™ eye bank to UT-Southwestern. At UT-Southwestern, tissues were repacked with fresh wet ice and returned overnight to the LIONS VISIONGIFT™ eye bank for analysis.

Example 11—Endothelial Cell Viability Analysis

Cell loss due to pre-stripping alone: pre-stripped grafts lying flat on the underlying stroma were stained with Calcein-AM (2.5 µg/mL; THERMOFISHER™, Grand Island, N.Y., USA) for 40 minutes at room temperature. Grafts were gently rinsed with BSS PLUS® prior to trephination using a 9.5 mm Hessburg-Barron trephine. The graft and underlying stroma were transferred onto a glass slide containing a bed of viscoelastic (OCCULON™; USIOL™, Lexington, Ky., USA) for image acquisition. Only the 8.0 mm central region of the graft was analyzed to exclude trephination damage which is not part of the pre-stripping process.

Cell loss of preloaded DMEK grafts: preloaded grafts were injected into a bed of Calcein-AM infused viscoelastic on a microscope slide. Calcein-AM at 12.5 µg/mL was mixed with OCCULON™ at a ratio of 4:1 to make a final cocktail of 2.5 µg/mL Calcein-AM+80% viscoelastic. Grafts were unfurled in this mixture and left to continue staining for 40 minutes prior to image acquisition.

All grafts were imaged using an XDY-1 inverted fluorescent microscope (ALLTION®, Wuzhou, China). For each graft, approximately 20-30 images were acquired at 20× magnification and stitched together using ADOBE PHOTO-SHOP ELEMENTS™ 7.0 software (ADOBE SYSTEMS™, San Jose, Calif., USA). Cell viability analysis was performed using Trainable Weka Segmentation in FIJI (see Schindelin J, et al. *Nat Methods.* 2012; 9:676-682) as previously described (see Jardine G J, et al. *Curr Eye Res.* 2014; 39:894-901 and Schallhorn J M, et al. *Cornea.* 2016; 35:377-382).

Example 12—Statistics

Descriptive values are shown as mean±standard deviation. Non-parametric Wilcoxon tests (see Wilcoxon F. *J Econ Entomol.* 1946; 39:269) were used to determine statistical significance, which is defined as $p<0.05$. Statistical analysis was performed using R Statistical Software (see R: A language and environment for statistical computing. [computer program]. Vienna, Austria: R Foundation for Statistical Computing; 2010; version 3.2.4).

Example 13—Donor Tissue and Tissue Preparation

Examples 13-16 describe a second study (Study 2). DMEK quality corneas used for this research were deemed unsuitable for transplant due to medical rule-outs other than endothelial pathology, and consent for research was obtained for all tissues.

DMEK grafts used for ECL analysis were prepared using previously described protocols for stripping (see Holiman J, et al. An Eye Bank DMEK Tissue Preperation Program for Corneas Stored at 4° C. In: Mohit Parekh.; Stefano Ferrari D P, ed. *Eye Banking*: Nova Biomedical; 2015:123-139; and Veldman P B, et al. *Cornea.* 2015; 34:1175-1178) and for preloading (see Tran K D, et al. *Cornea.* 2017; 36:484-490) by the same trained Research Fellow. Grafts that were shipped to Weill Cornell Medical College were prepared by trained eye bank technicians at LIONS VISIONGIFT™. All grafts were punched with an 8.0 mm Barron Hessburg trephine (BARRON PRECISION INSTRUMENTS™). Grafts were stained for 15 seconds with 0.06% Trypan blue (C-Blue; STEPHENS INSTRUMENTS™, Lexington, Ky.) to visualize complete trephination at the graft edges. Peripheral Descemet membrane was removed, and the grafts were separated from the corneoscleral cap with micro-forceps and laid back down on the fluid coated stromal bed.

Five pairs of corneas were used in experiments comparing preloaded DMEK grafts that were unstained and preloaded DMEK grafts that were prestained with Trypan blue. For the unstained group, the grafts were allowed to scroll in the corneoscleral cap, which was filled with OPTISOL™-GS (BAUSCH & LOMB™, St. Louis, Mo.) prior to loading into a Straiko modified Jones tube (GUNTHER WEISS SCIENTIFIC GLASS™, Hillsboro, Oreg.). The mate corneas were stained with Trypan blue solution filling the corneoscleral cap for 4 minutes. After staining, the Trypan blue was diluted and replaced with OPTISOL™-GS and the scrolls were suctioned up from the corneoscleral cap into a Straiko modified Jones tube. All Straiko modified Jones tubes containing the preloaded grafts (stained and unstained) were submerged in 20 mL of OPTISOL™-GS, docked between the support posts of the viewing chamber (KROLMAN™, Boston, Mass.) and stored for 3 days at 4° C. prior to analysis.

Five unstained and preloaded grafts were stained inside of the Straiko modified Jones tube after 3 days in cold storage. BSS (ALCON®, Fort Worth, Tex.) from a petri dish was drawn into the injector to replace the OPTISOL™-GS in the modified Jones tubes. The grafts were moved towards the tip of the injector and stained with Trypan blue (0.06%) for 4 minutes (see FIGS. 10 and 11). After 4 minutes, more BSS was drawn into the injector to dilute the Trypan blue. Further dilutions were possible by moving the plunger of the injector back and forth to promote fluid exchange with new BSS.

Example 14—Endothelial Cell Viability Analysis

Straiko modified Jones tubes were removed from the viewing chamber and the Straiko injector was assembled as previously described (see Terry M A, et al. *Cornea.* 2015; 34:845-852). DMEK grafts were ejected onto a microscope slide coated with a mixture of Calcein-AM (BIOTIUM™, Fremont, Calif.) and viscoelastic (OCCULON™; STEPHENS INSTRUMENTS™, Lexington, Ky.) comprised of 2.5 µg/mL Calcein-AM+80% viscoelastic. Grafts were unscrolled using viscoelastic as previously described (see Tran K D, et al. *Cornea.* 2017; 36:484-490 and Schallhorn J M, et al. *Cornea.* 2016; 35:377-382) and stained in the mixture for 40 minutes.

Stained grafts were imaged on an XDY-1 inverted fluorescent microscope by K. T.) (ALLTION®). Approximately 30 images were acquired per graft at 20× magnification, and the individual images were assembled using ADOBE PHOTOSHOP ELEMENTS™ 14.0 software (ADOBE SYSTEMS™). ECL was quantified as previously described using Trainable Weka Segmentation in FIJI (see Schallhorn J M, et al. *Cornea.* 2016; 35:377-382; Jardine G J, et al. *Curr Eye Res.* 2014; 39:894-901; and Schindelin J, et al. *Nat Methods.* 2012; 9:676-682). All grafts were randomized and analyzed by 2 readers who were masked to the treatment of the grafts (unstained, prestained, and stained inside of the injector). The values reported in this study are the average from the 2 readers, and their readings were not significantly different from each other (P=0.3).

Example 15—Statistical Analysis

R Statistical Software, version 3.2.4, (see *R: A language and environment for statistical computing.* [computer program]. Vienna, Austria: R Foundation for Statistical Computing; 2010) was employed for statistical analysis. Descriptive values are shown as mean±standard deviation. Non-parametric Wilcoxon tests were used to determine statistical significance which was defined as P<0.05.

Example 16—Evaluation of Prestained Grafts after Cross-Country Shipping

Eight additional prestained and preloaded grafts (containing S-stamps) were shipped to Weill Cornell Medical College and examined by an experienced DMEK corneal surgeon, 1 or 3 days after preparation. Prior to shipping, the color saturation of the stained grafts was measured using a reference serial dilution series $(1/2)^X$ of Trypan blue (see FIG. 12A). Here, X is the number of dilutions such that dilution 0 is the original concentration of 0.06% Trypan blue, dilution #1 equals ½ of the original Trypan concentration (FIG. 12A, panel 1), and dilution #2 is ¼ of the original concentration (FIG. 12A, panel 2), and so on. Trypan dilutions were imaged using a ZEISS™ OPMIMD S-5 microscope (ZEISS™, Thornwood, N.Y.) equipped with an OPTRONICS® MICROCAST® HD digital camera (OPTRONICS®, Goleta, Calif.), and the reference was assembled using ADOBE PHOTOSHOP™ CS6 (ADOBE SYSTEMS™). The color saturation of the grafts was assessed again using the same reference standards prior to injection into donor eyes. For the simulated DMEK surgery using grafts prepared and shipped 3 days prior, the Straiko modified Jones tubes containing the grafts were assembled as previously described (see Terry M A, et al. *Cornea.* 2015; 34:845-852), and the grafts were injected into the donor eyes and opened using standard techniques (see Liarakos V S, et al. *JAMA Ophthalmol.* 2013; 131:29-35 and Yoeruek E, et al. *Cornea.* 2013; 32:370-373).

Example 17—Testing Silicone Caps

A closed silicone cap was coupled to one end of a first Jones tube such that the first corneal tissue carrier had one opening to the surrounding OPTISOL™. An open silicone cap (i.e., a cap having a 1 mm opening) was coupled to one end of a second Jones tube such that the second corneal tissue carrier has two openings to the surrounding OPTISOL™.

In order to test for the maximum potential damage a cap might induce, preloaded grafts were allowed to settle on the silicone caps and the grafts were stored at 4° C. for 5 days. After 5 days of storage, all grafts were stained with Calcein-AM (a cell viability stain) and cell viability was examined. All grafts were viable and no significant cell death patterns were observed associated with a graft settling on a cap.

Additional grafts were preloaded in Jones tubes with the closed silicone caps at the LIONS VISIONGIFT™ eye bank in Portland, Oreg. and shipped to Cornell University in New York City, N.Y. via plane. The position of the grafts inside the Jones tubes was examined upon arrival at Cornell University. Of the grafts received and examined, the grafts remained in the cavity of the Jones tubes, and the caps remained attached to Jones tubes after cross-country shipping.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially transparent" is recited with respect to a feature, it is understood that in further embodiments, the feature can have a precisely transparent configuration.

Numerous references have been made to printed publications throughout this specification. Each of the above-cited references and printed publications is individually incorporated herein by reference in its entirety.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An assembly for storing and evaluating corneal tissue, the assembly comprising:
a viewing chamber comprising a body and a lid; and
a corneal tissue carrier removably coupled to an inner portion of the body of the viewing chamber.

2. The assembly of claim 1, further comprising:
a corneal tissue sample disposed within an inner cavity of the corneal tissue carrier.

3. The assembly of claim 2, wherein the corneal tissue sample is a stained corneal tissue sample.

4. The assembly of claim 2, wherein the corneal tissue carrier further comprises a first opening disposed at a first end of the corneal tissue carrier.

5. The assembly of claim 4, wherein the corneal tissue carrier further comprises a second opening disposed at a second end of the corneal tissue carrier.

6. The assembly of claim 5, wherein a second cap or plug is removably coupled to the corneal tissue carrier at the second opening, and wherein the second cap or plug inhibits passage of the corneal tissue sample out of the inner cavity of the corneal tissue carrier.

7. The assembly of claim 6, wherein the second cap or plug allows passage of fluid into and out of the inner cavity of the corneal tissue carrier.

8. The assembly of claim 6, wherein the second cap or plug inhibits passage of fluid into and out of the inner cavity of the corneal tissue carrier.

9. The assembly of claim 4, wherein a first cap or plug is removably coupled to the corneal tissue carrier at the first opening of the corneal tissue carrier, wherein the first cap or plug inhibits passage of the corneal tissue sample out of the inner cavity of the corneal tissue carrier.

10. The assembly of claim 9, wherein the first cap or plug allows passage of fluid into and out of the inner cavity of the corneal tissue carrier.

11. The assembly of claim 9, wherein the first cap or plug inhibits passage of fluid into and out of the inner cavity of the corneal tissue carrier.

12. The assembly of claim 2, further comprising:
a fluid disposed within the inner cavity of the corneal tissue carrier such that the corneal tissue sample is substantially immersed in the fluid.

13. The assembly of claim 12, wherein the fluid is a preservation fluid.

14. The assembly of claim 2, wherein the body of the viewing chamber comprises a plurality of arms extending from an inner surface of the body, the plurality of arms configured to removably couple the corneal tissue carrier to the inner portion of the body.

15. The assembly of claim 2, wherein at least a portion of each of the viewing chamber and the corneal tissue carrier is substantially transparent such that the corneal tissue sample is visible to a user.

16. The assembly of claim 2, wherein the corneal tissue carrier is a Straiko modified Jones tube.

17. The assembly of claim 16, wherein the length of the corneal tissue carrier is about 38 mm.

18. A corneal tissue sample assembly, comprising:
(i) a corneal tissue carrier comprising an inner cavity, a first opening disposed at a first end of the corneal tissue carrier, and a second opening disposed at a second end of the corneal tissue carrier;
(ii) a first cap or plug; and
(iii) a second cap or plug,
wherein the first cap or plug is removably coupled to the corneal tissue carrier at the first opening and the second cap or plug is removably coupled to the corneal tissue carrier at the second opening.

19. The assembly of claim 18, further comprising a corneal tissue sample disposed within the inner cavity of the corneal tissue carrier.

20. The assembly of claim 19, wherein the corneal tissue sample is a stained corneal tissue sample.

21. The assembly of claim 19, further comprising:
a fluid disposed within the inner cavity of the corneal tissue carrier such that the corneal tissue sample is substantially immersed in the fluid.

22. The assembly of claim 21, wherein the fluid is a preservation fluid.

23. A method of processing a corneal tissue sample, the method comprising:
obtaining a corneal tissue sample;
disposing the corneal tissue sample in an inner cavity of a corneal tissue carrier; and
coupling the corneal tissue carrier to an inner portion of a viewing chamber.

24. The method of claim 23, further comprising:
filling at least a portion of the inner cavity of the corneal tissue carrier with a fluid such that the corneal tissue sample is substantially immersed in the fluid.

25. The method of claim 23, further comprising:
evaluating the corneal tissue sample disposed within the corneal tissue carrier and the viewing chamber.

26. The method of claim 25, wherein evaluating the corneal tissue sample comprises using at least one of slit-lamp biomicroscopy, specular microscopy, light microscopy, and optical coherence tomography.

27. The method of claim 25, wherein evaluating the corneal tissue sample comprises at least one of determining endothelial cell density (ECD) of the corneal tissue sample and estimating a percentage of endothelial cell loss (ECL) of the corneal tissue sample.

28. The method of claim 27, further comprising:
rejecting the corneal tissue sample when the ECD is below about 2000 cells/mm$^2$.

29. The method of claim 27, further comprising:
rejecting the corneal tissue sample when the estimated percentage of ECL is above about 20%.

30. The method of claim 23, further comprising:
coupling a cap or plug to an opening of the corneal tissue carrier subsequent to disposing the corneal tissue sample in the inner cavity of the corneal tissue carrier such that passage of the corneal tissue sample out of the corneal tissue carrier is inhibited.

* * * * *

(12) EX PARTE REEXAMINATION CERTIFICATE (11642nd)
United States Patent
Tran

(10) Number: US 10,041,865 C1
(45) Certificate Issued: Feb. 14, 2020

(54) CORNEAL TISSUE SAMPLE ASSEMBLIES AND RELATED METHODS OF USE

(71) Applicant: Lions VisionGift, Portland, OR (US)

(72) Inventor: Khoa D. Tran, Portland, OR (US)

(73) Assignee: Lions VisionGift

Reexamination Request:
No. 90/014,279, Mar. 30, 2019

Reexamination Certificate for:
Patent No.: 10,041,865
Issued: Aug. 7, 2018
Appl. No.: 15/874,789
Filed: Jan. 18, 2018

Related U.S. Application Data

(63) Continuation of application No. 15/660,004, filed on Jul. 26, 2017.

(60) Provisional application No. 62/407,930, filed on Oct. 13, 2016.

(51) Int. Cl.
| | |
|---|---|
| *G01N 1/28* | (2006.01) |
| *G01N 21/03* | (2006.01) |
| *G01N 15/10* | (2006.01) |
| *G01N 15/14* | (2006.01) |

(52) U.S. Cl.
CPC ............. *G01N 1/28* (2013.01); *G01N 15/10* (2013.01); *G01N 21/03* (2013.01); *G01N 2015/1006* (2013.01); *G01N 2015/1486* (2013.01); *G01N 2021/0342* (2013.01)

(58) Field of Classification Search
None
See application file for complete search history.

(56) References Cited

To view the complete listing of prior art documents cited during the proceeding for Reexamination Control Number 90/014,279, please refer to the USPTO's public Patent Application Information Retrieval (PAIR) system under the Display References tab.

*Primary Examiner* — Ling X Xu

(57) ABSTRACT

Assemblies for storing, handling, transporting, viewing, evaluating, and/or shipping corneal tissue are provided. The assemblies may include a viewing chamber and a corneal tissue carrier removably coupled to an inner portion of the viewing chamber. The assemblies may further include a corneal tissue sample disposed within the corneal tissue carrier. Methods of processing a corneal tissue sample and administering the corneal tissue sample to a subject are also provided.

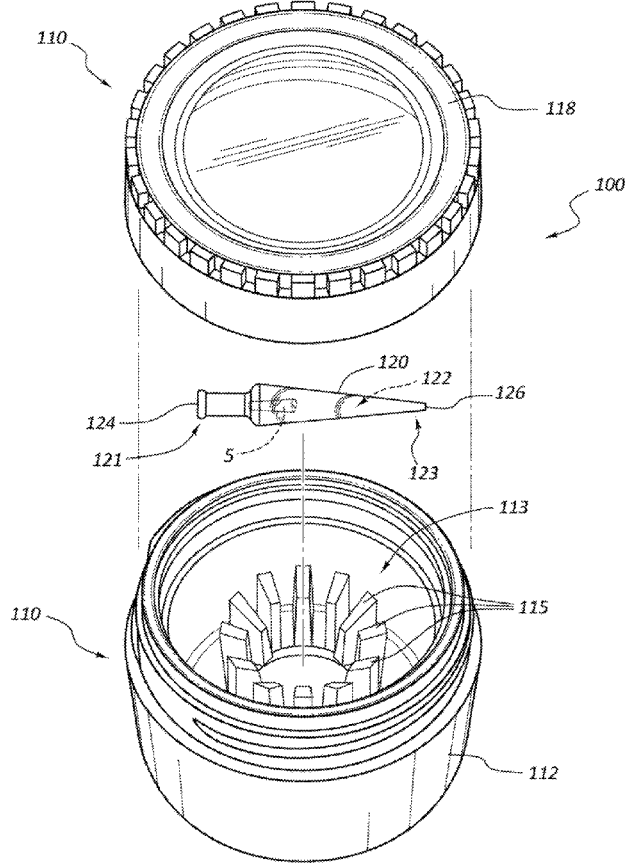

US 10,041,865 C1

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 18-22 are cancelled.

Claims 1, 16 and 23 are determined to be patentable as amended.

Claims 2-15, 17 and 24-30, dependent on an amended claim, are determined to be patentable.

New claims 31-35 are added and determined to be patentable.

1. An assembly for storing and evaluating corneal tissue, the assembly comprising:
   a viewing chamber comprising a body and a lid; and
   a corneal tissue carrier *comprising a tube having a portion that is substantially transparent, wherein the corneal tissue carrier is* removably coupled to an inner portion of the body of the viewing chamber.

16. [The assembly of claim 2.] *An assembly for storing and evaluating corneal tissue, the assembly comprising:*
    *a viewing chamber comprising a body and a lid;*
    *a corneal tissue carrier removably coupled to an inner portion of the body of the viewing chamber; and*
    *a corneal tissue sample disposed within an inner cavity of the corneal tissue carrier;*
    wherein the corneal tissue carrier is a Straiko modified Jones tube.

23. A method of processing a corneal tissue sample, the method comprising:
    obtaining a corneal tissue sample;
    disposing the corneal tissue sample in an inner cavity of a corneal tissue carrier *comprising a tube having a portion that is substantially transparent*; and
    coupling the corneal tissue carrier to an inner portion of a viewing chamber comprising a body and a lid.

31. *The method of claim 23, wherein the tube is a Jones tube.*

32. *The method of claim 31, wherein the Jones tube is a Straiko modified Jones tube.*

33. *The assembly of claim 1, wherein the tube is a Jones tube.*

34. *The assembly of claim 33, wherein the Jones tube is a Straiko modified Jones tube.*

35. *The assembly of claim 1, wherein:*
    *the body has a base having an outer perimeter and a substantially transparent portion, a sidewall extending from the outer perimeter to an upper rim, a radial arrangement of a plurality of arms extending from an inner surface of the base; wherein the substantially transparent portion of the base is defined within the radial arrangement of a plurality of arms;*
    *the lid having a substantially transparent portion, wherein the lid is configured to form a fluid tight seal about the upper rim of the body, and*
    *wherein the tube is configured to be removably coupled between adjacent arms in the radial arrangement of the plurality of arms to hold the tube in the inner portion of the body of the viewing chamber.*

* * * * *